US010399594B2

United States Patent
Goto et al.

(10) Patent No.: US 10,399,594 B2
(45) Date of Patent: Sep. 3, 2019

(54) POWER STEERING DEVICE AND DEVICE FOR CONTROLLING POWER STEERING DEVICE

(71) Applicant: HITACHI AUTOMOTIVE SYSTEMS, LTD., Hitachinaka-shi, Ibaraki (JP)

(72) Inventors: Makoto Goto, Isehara (JP); Mitsuo Sasaki, Hadano (JP)

(73) Assignee: HITACHI AUTOMOTIVE SYSTEMS, LTD., Hitachinaka-Shi (JP)

( * ) Notice: Subject to any disclaimer, the term of this patent is extended or adjusted under 35 U.S.C. 154(b) by 45 days.

(21) Appl. No.: 15/742,104

(22) PCT Filed: May 16, 2016

(86) PCT No.: PCT/JP2016/064478
§ 371 (c)(1),
(2) Date: Jan. 5, 2018

(87) PCT Pub. No.: WO2017/006623
PCT Pub. Date: Jan. 12, 2017

(65) Prior Publication Data
US 2018/0194390 A1    Jul. 12, 2018

(30) Foreign Application Priority Data
Jul. 8, 2015 (JP) ................. 2015-136565

(51) Int. Cl.
*B62D 5/04* (2006.01)
*B62D 6/00* (2006.01)
(Continued)

(52) U.S. Cl.
CPC .......... *B62D 5/0487* (2013.01); *B62D 5/046* (2013.01); *B62D 5/0481* (2013.01);
(Continued)

(58) Field of Classification Search
CPC .... B62D 5/046; B62D 5/0481; B62D 5/0484; B62D 5/0487; B62D 6/00; G01L 5/221; G01N 27/121
See application file for complete search history.

(56) References Cited

FOREIGN PATENT DOCUMENTS

JP    2006-130959 A    5/2006
JP    2008-037255 A    2/2008
(Continued)

*Primary Examiner* — Redhwan K Mawari
(74) *Attorney, Agent, or Firm* — Foley & Lardner LLP

(57) ABSTRACT

A device for controlling a power steering device having: a steering mechanism for transmitting the rotation of a steering wheel to steered wheels; an electric motor for imparting steering force to the steering mechanism; a transmission mechanism for transmitting the rotational force of the motor to the steering mechanism; a housing for accommodating at least part of the steering mechanism, the transmission mechanism, and the motor; a water sensor for detecting moisture in the housing; and a torque sensor for detecting steering torque; wherein the control device is provided with a first fault assessment unit for assessing faults in the power steering device on the basis of a steering torque signal, etc., and a second fault assessment unit for assessing faults in the power steering device when the water sensor has sensed moisture. It is thereby possible to assess faults in the power steering device from a multifaceted perspective.

18 Claims, 23 Drawing Sheets

(51) Int. Cl.
   *G01L 5/22*  (2006.01)
   *G01N 27/12*  (2006.01)

(52) U.S. Cl.
   CPC .............. *B62D 5/0484* (2013.01); *B62D 6/00* (2013.01); *G01L 5/221* (2013.01); *G01N 27/121* (2013.01)

(56) References Cited

FOREIGN PATENT DOCUMENTS

| | | |
|---|---|---|
| JP | 2008-178270 A | 7/2008 |
| JP | 2009-023402 A | 2/2009 |
| JP | 2014-234102 A | 12/2014 |

FREQUENCY: 20-25 Hz
(STEERING SPEED: 30 DEGREES/SECOND)

FREQUENCY: 20-25 Hz
(STEERING SPEED: 30 DEGREES/SECOND)

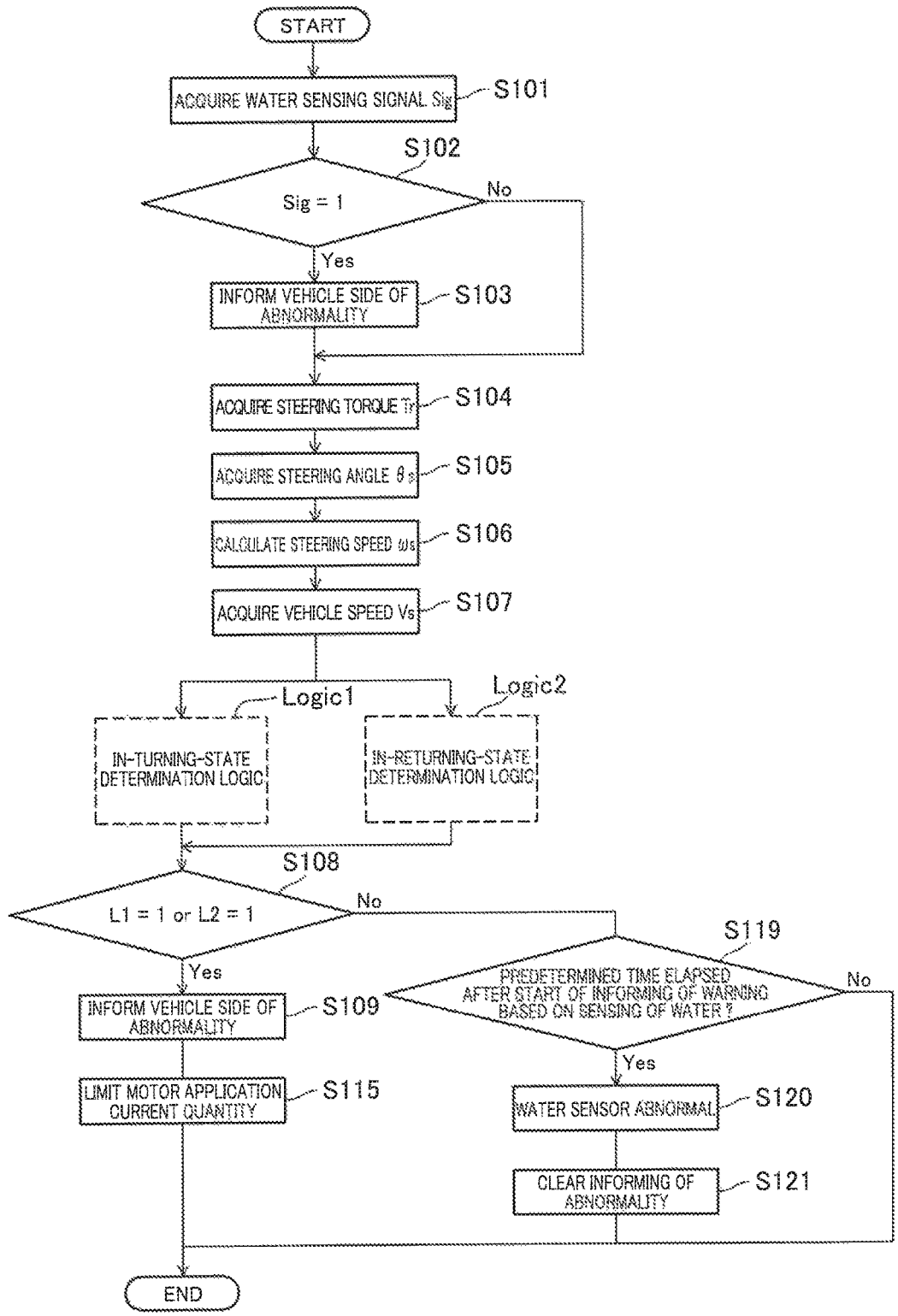

POWER STEERING DEVICE AND DEVICE FOR CONTROLLING POWER STEERING DEVICE

TECHNICAL FIELD

The present invention relates to a power steering device and a power steering device control device for application to a vehicle.

BACKGROUND ART

A patent document 1 discloses a known conventional power steering device as follows.

This power steering device includes a power transmission mechanism configured to transmit a torque of an electric motor to a rack bar while converting the torque into an axial moving force of the rack bar. The power steering device includes a housing liquid-tightly covering an outer periphery pf the rack bar and the power transmission mechanism. When water enters an interior of the housing, the power steering device determines that the power steering device is abnormal, based on detection of the entrance of water by a water sensor disposed in the housing.

However, the conventional power steering device is confronted with a problem where the power steering device is capable of detecting the entrance of water into the housing by the water sensor, but is incapable of performing sufficient abnormality determination, for example, when foreign matter such as sand or dust other than water enters the interior of the housing, because of incapability of detecting such foreign matter.

PRIOR ART DOCUMENT(S)

Patent Document(s)

Patent Document 1: JP 2014-234102 A

SUMMARY OF THE INVENTION

The present invention has been made with attention to the technical problem described above, and is targeted for providing a power steering device and a power steering device control device capable of determining abnormality of the power steering device from multiple viewpoints.

Among other things, the present invention is characterized by including: a steering mechanism configured to transmit rotation of a steering wheel to a steered wheel; an electric motor configured to apply a steering force to the steering mechanism; a transmission mechanism disposed between the steering mechanism and the electric motor, and configured to transmit a torque of the electric motor to the steering mechanism; a housing configured to accommodate the transmission mechanism, the electric motor, and at least part of the steering mechanism; a water sensing element disposed in the housing, and configured to sense water in the housing; a torque sensor configured to sense a steering torque occurring in the steering mechanism; a first abnormality determination part configured to determine that the power steering device is abnormal, based on one of the signals of the steering torque, the rotational speed of the electric motor, and the steering speed; and a second abnormality determination part configured to determine that the power steering device is abnormal, in response to detection of water by the water sensing element.

The present invention makes it possible to determine abnormality of the power steering device from multiple viewpoints.

BRIEF DESCRIPTION OF THE DRAWINGS

FIG. 23 is a flow chart showing an abnormality determination processing control of a power steering device according to an eighth embodiment.

MODE(S) FOR CARRYING OUT THE INVENTION

The following describes a power steering device and a power steering device control device according to embodiments of the present invention in detail with reference to the drawings.

<First Embodiment>

First, the following describes system configuration of the power steering device with reference to FIGS. 1 to 5.

Figure 1:
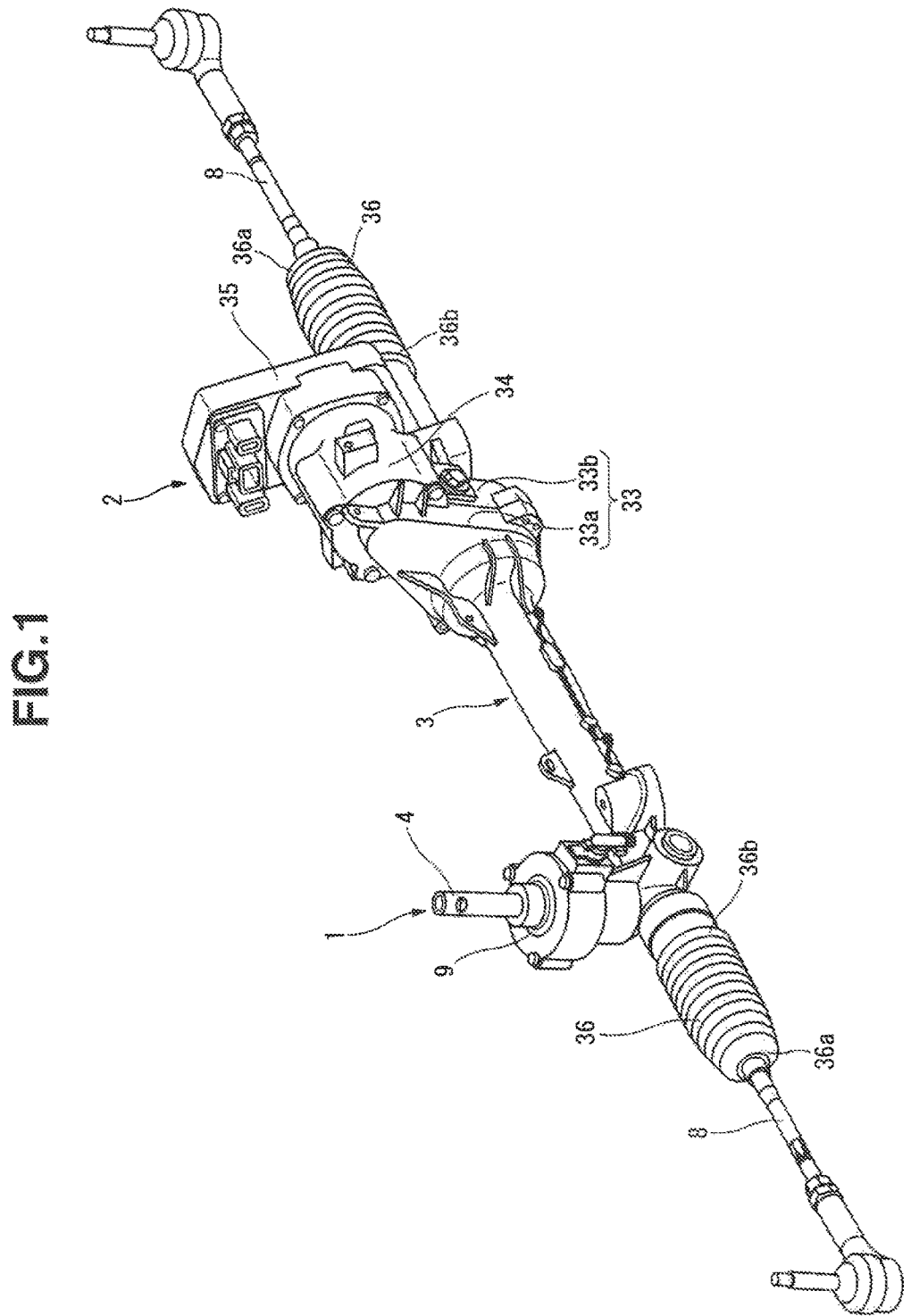
FIG. 1 is a perspective view showing a power steering device according to a first embodiment of the present invention.
Figure 2:
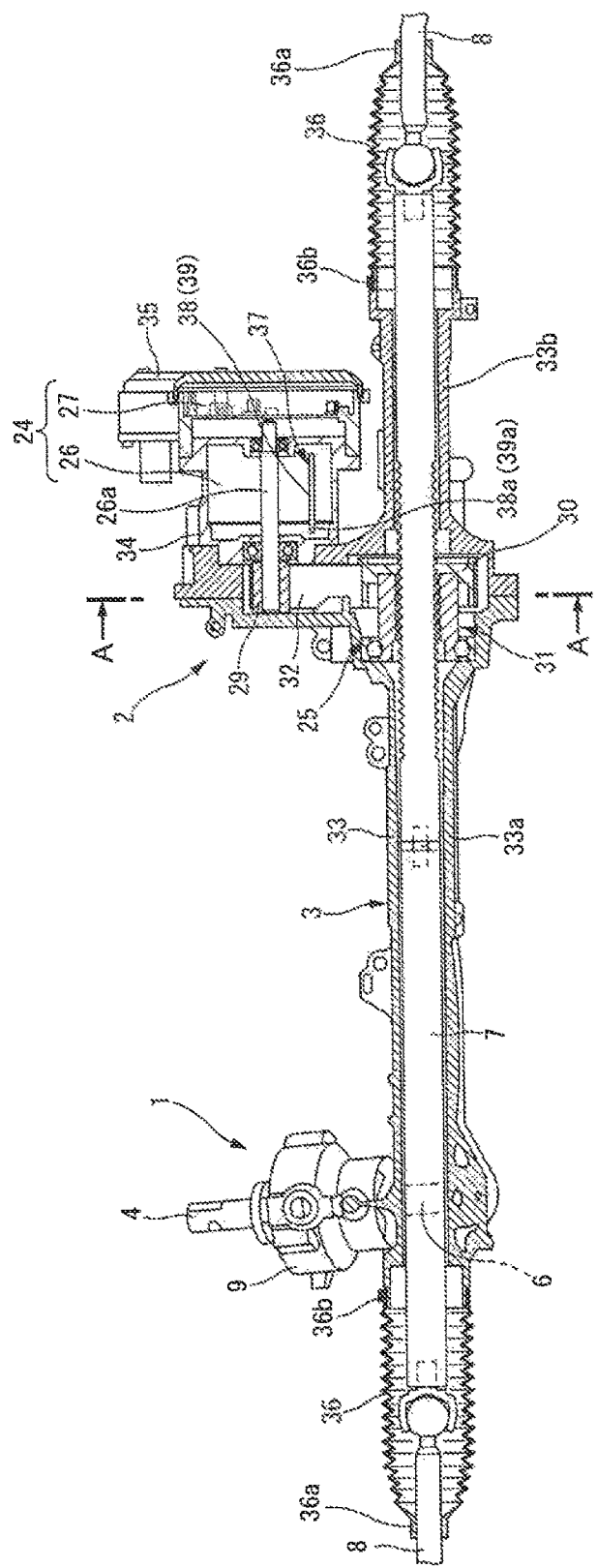
FIG. 2 is a longitudinal sectional view of the power steering device.

As shown in FIGS. 1 and 2, the power steering device includes a steering mechanism 1, a steering assist mechanism 2, and a housing 3, wherein steering mechanism 1 is configured to transmit rotation of a steering wheel not shown to steered wheels not shown, wherein steering assist mechanism 2 is configured to assist steering operation of a driver by applying a steering assist force to steering mechanism 1, based on information about steering and others, and wherein part of steering mechanism 1 and part of steering assist mechanism 2 are accommodated in housing 3.

As shown in FIG. 2 in particular, steering mechanism 1 generally includes an input shaft 4, an output shaft 6, and a rack bar 7, wherein input shaft 4 includes a first end side linked to the steering wheel in a manner to rotate integrally with the steering wheel, wherein output shaft 6 includes a first end side coupled to input shaft 4 via a torsion bar 5 (see FIG. 3) in a manner to rotate with respect to input shaft 4, and wherein rack bar 7 includes an outer periphery formed with rack teeth not shown meshed with a pinion gear 6a of an outer periphery of a second end portion of output shaft 6 (see FIGS. 3 and 4), and is configured to travel in an axial direction of rack bar 7. Rack bar 7 includes end portions linked to the steered wheels via tie rods 8, 8, knuckle arms not shown, etc., respectively, and is configured to change orientation of each steered wheel by pulling the corresponding knuckle arm by axial movement of rack bar 7.

A torque sensor 10 and a steering angle sensor 11 are provided in a sensor housing 9 accommodating the input shaft 4 and output shaft 6, wherein torque sensor 10 is configured to sense a steering torque in steering mechanism 1 which is caused by driver's steering operation, and wherein steering angle sensor 11 is configured to sense a steering angle that is a quantity of rotation of the steering wheel from its neutral position.

Figure 3:
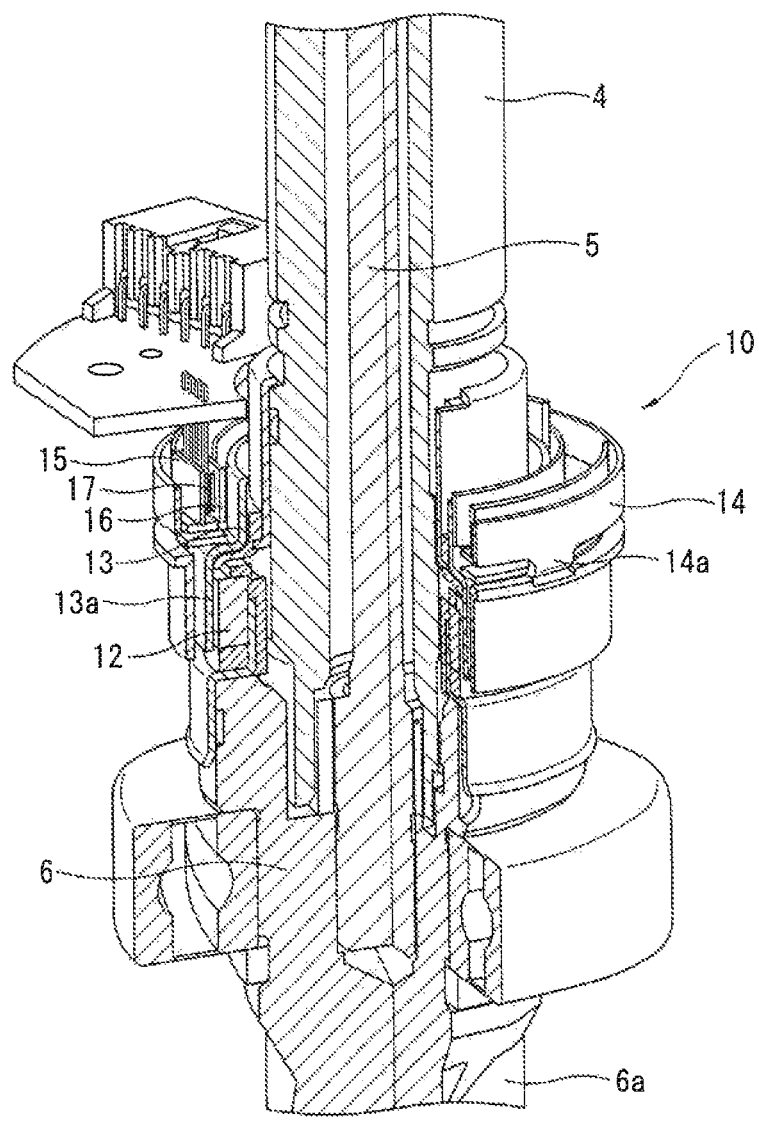
FIG. 3 is a partial sectional view of a torque sensor according to the first embodiment.

As shown in FIG. 3, torque sensor 10 includes: a permanent magnet 12 provided at output shaft 6 in a manner to rotate integrally with output shaft 6, wherein permanent magnet 12 has an annular shape where different magnetic poles are alternately arranged in a circumferential direction; inner and outer yoke members 13, 14 in pairs, each of which has an annular shape and includes a lower part formed with a plurality of nail portions 13a, 14a facing an outer peripheral surface of permanent magnet 12; first and second magnetism collection rings 15, 16 in outer and inner pairs, each of which is disposed between yoke members 13, 14, and is configured to generate a magnetic field inside, based on a magnetic field of permanent magnet 12 flowing between magnetic poles adjacent to each other via nail portions 13a, 14a; a magnetic sensor 17 including main and auxiliary Hall elements 17a, 17b in pairs (see FIGS. 6 and 7) which are disposed between magnetism collection rings 15, 16 for sensing a change of an internal magnetic field between magnetism collection rings 15, 16.

Permanent magnet 12 is configured such that as an angular difference of permanent magnet 12 with respect to yoke members 13, 14 increases, namely, as a torsional angle of torsion bar 5 increases, the magnetic flux density of the magnetic field flowing between magnetic poles adjacent to each other via nail portions 13a, 14a Increases. As this magnetic flux density increases, the magnetic flux density of the internal magnetic field between magnetism collection rings 15, 16 increases. Torque sensor 10 is configured to sense the steering torque by sensing a change of the magnetic flux density of the internal magnetic field between magnetism collection rings 15, 16, based on the Hall effect of the Hall elements of magnetic sensor 17.

Figure 4:
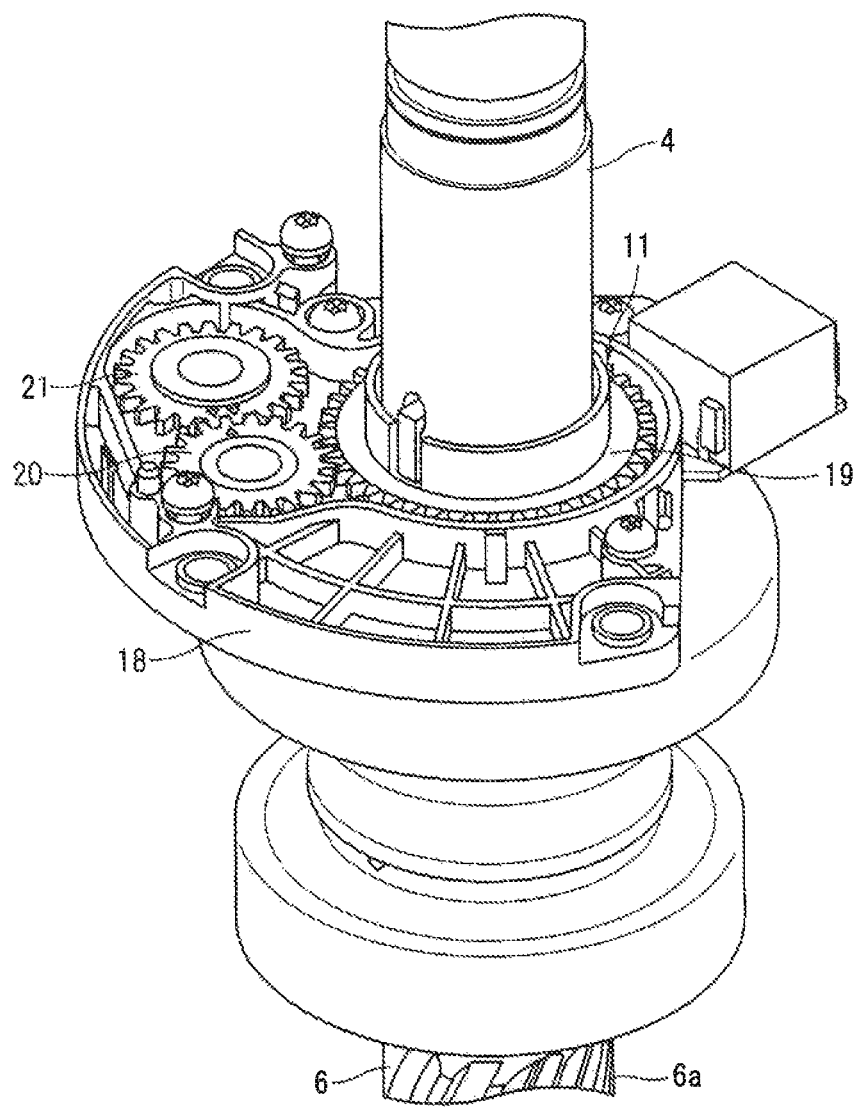
FIG. 4 is a perspective view showing internal configuration of a steering angle sensor according to the first embodiment.

As shown in FIG. 4, steering angle sensor 11 includes: a gear wheel 19 arranged in a casing 18, and provided at the outer periphery of input shaft 4 in a manner to rotate integrally with input shaft 4, wherein casing 18 forms a part of sensor housing 9; a first pinion 20 configured to rotate in mesh with gear wheel 19; and a second pinion 21 configured to rotate in mesh with first pinion 20, wherein second pinion 21 has a different tooth number than the first pinion.

Main and auxiliary first MR elements 22a, 23a in pairs (see FIG. 7) are provided above first pinion 20, and configured to sense a rotation angle of first pinion 20 (first rotation angle), whereas main and auxiliary second MR elements 22b, 23b (see FIG. 7) are provided above second pinion 21, and configured to sense a rotation angle of second pinion 21 (second rotation angle). Main MR elements 22a, 22b form a main steering angle sensing element 22 (see FIG. 6), whereas auxiliary MR elements 23a, 23b form an auxiliary steering angle sensing element 23 (see FIG. 6).

Each steering angle sensing element 22, 23 is configured to sense the steering angle that is the quantity of rotation of the steering wheel form its neutral position, based on the angular difference between the first and second rotation angles sensed by the corresponding MR elements 22a, 22b, 23a, 23b.

As shown in FIG. 2, steering assist mechanism 2 includes: a motor unit 24 configured to output a steering assist force, depending on a result of sensing of torque sensor 10 and steering angle sensor 11; and a transmission mechanism (speed reducer) 25 configured to transmit the steering assist force (torque) to rack bar 7 while converting the steering assist force into an axial moving force of rack bar 7 with speed reduction.

Motor unit 24 is an integral unit of an electric motor 26 and an ECU 27, wherein electric motor 26 is configured to rotate an input pulley 29 described below, and thereby apply the steering assist force to rack bar 7 via transmission mechanism 25, and wherein ECU 27 is attached to electric motor 26, and is configured as a control device to control driving of electric motor 26 depending on parameters such as the steering torque and vehicle speed.

Electric motor 26 is a so-called brushless DC motor, wherein ECU 27 is provided with a motor rotation angle sensor 28 including main and auxiliary angle sensing elements 28a, 28b in pairs (see FIGS. 6 and 7) configured to sense a rotation angle of a rotor not shown of electric motor 26.

Figure 5:
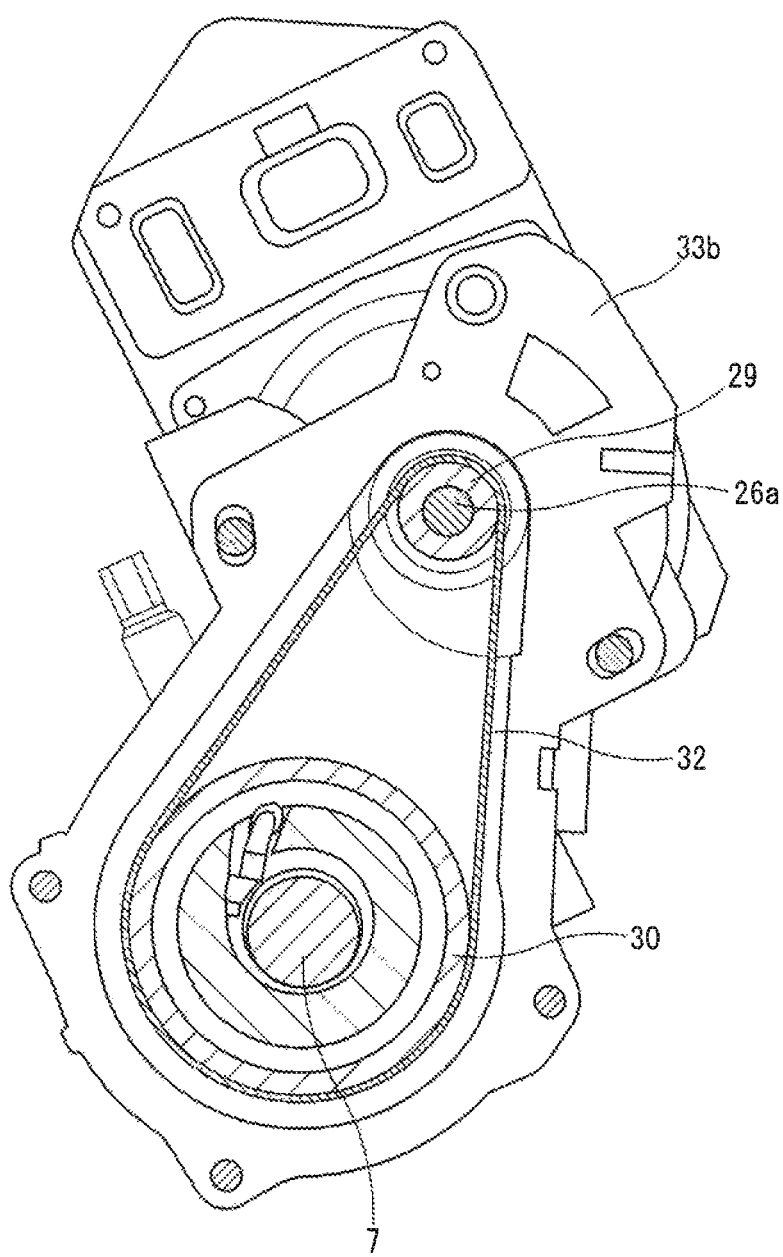
FIG. 5 is a sectional view taken along a line A-A in FIG. 2.

As shown in FIGS. 2 and 5, transmission mechanism 25 includes: Input pulley 29 provided at an outer peripheral side of an output shaft 26a of electric motor 26 in a manner to rotate integrally with output shaft 26a about an axis of output shaft 26a; an output pulley 30 provided at the outer periphery of rack bar 7 in a manner to rotate with respect to rack bar 7, and configured to rotate about an axis of rack bar 7 based on a torque of input pulley 29; a ball screw mechanism 31 disposed between output pulley 30 and rack bar 7, and configured to convert rotation of output pulley 30 into axial movement of rack bar 7 with speed reduction; and a belt 32 wound over the input and output pulleys 29, 30, and configured to transmit rotation of input pulley 29 to output pulley 30, and thereby serve for synchronized rotation of input and output pulleys 29, 30.

As shown in FIGS. 1 and 2, housing 3 generally includes: a gear housing 33 including first and second gear housing forming parts 33a, 33b separated in a vehicle lateral direction, wherein gear housing 33 is configured to accommodate rack bar 7 and transmission mechanism 25 as part of steering mechanism 1; a motor housing 34 configured to accommodate electric motor 26 inside; and an ECU housing 35 configured to accommodate ECU 27. Each housing 33-35 is opened at a part coupled to the adjacent housing so that the internal spaces of housings 33-35 communicate with each other through their openings.

Gear housing 33 includes end portions in the axial direction of rack bar 7, which are formed with respective openings, wherein boots 36, 36 are provided at the corresponding openings, wherein each boot 36 is accordion-fold. Each boot 36 includes a first end portion 36a attached to an outer peripheral surface of tie rod 8, and a second end portion 36b attached to an outer peripheral surface of gear housing 33, so as to prevent water, dust, etc. from entering the interior of housing 3.

A water sensor 37 is provided in housing 3, and configured as a water sensing element to sense water when the water enters the interior of the housing 3.

As shown in FIG. 2, water sensor 37 includes a pair of electrodes 38, 39 which are disposed in a lower part of the internal space of electric motor 26, and are arranged substantially parallel to output shaft 26a. Electrodes 38, 39 are arranged to be separated from each other with a slight clearance, wherein each electrode 38, 39 includes: a first end portion 38a, 39a that is closer to input pulley 29 and projects into the inside of motor housing 34; and a second end side connected electrically to ECU 27.

ECU 27 is configured to apply a voltage to electrode 38 of electrodes 38, 39 constantly or at constant intervals, and monitor the other electrode 39, and determine that water enters the interior of housing 3, in response to application of a voltage to electrode 39.

Specifically, when boot 36 is broken and water enters the housing 3 thorough a broken part of boot 36, the water is lifted by rotation of belt 32 to reach the water sensor 37 in motor housing 34, and establish electrical connection, and thereby allow electrode 38 to apply a voltage to electrode 39. This voltage is sensed by ECU 27, to determine that water enters the interior of housing 3.

Figure 6:
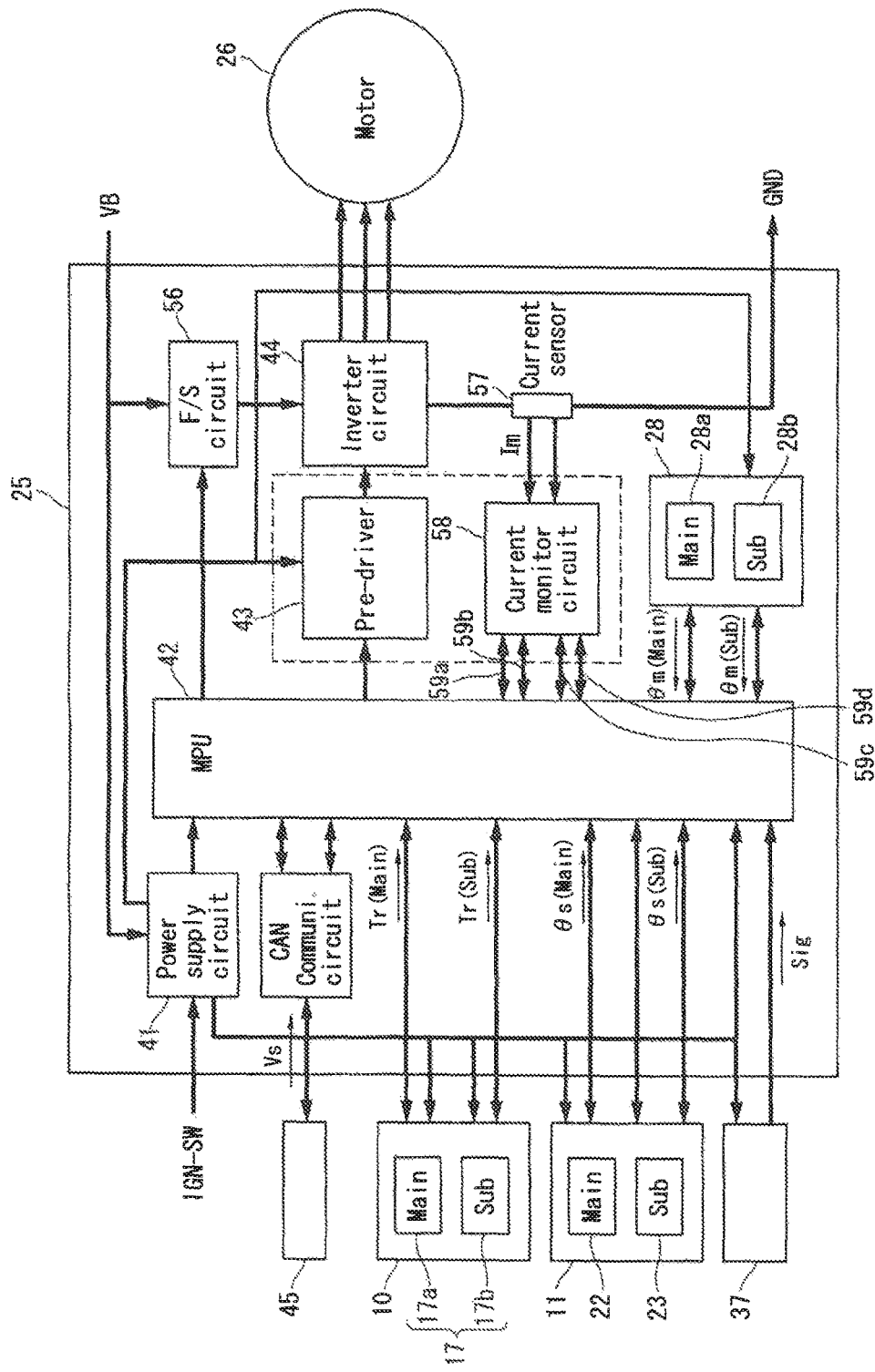
FIG. 6 is a block diagram showing configuration of an electrical system of an ECU according to the first embodiment.
Figure 7:
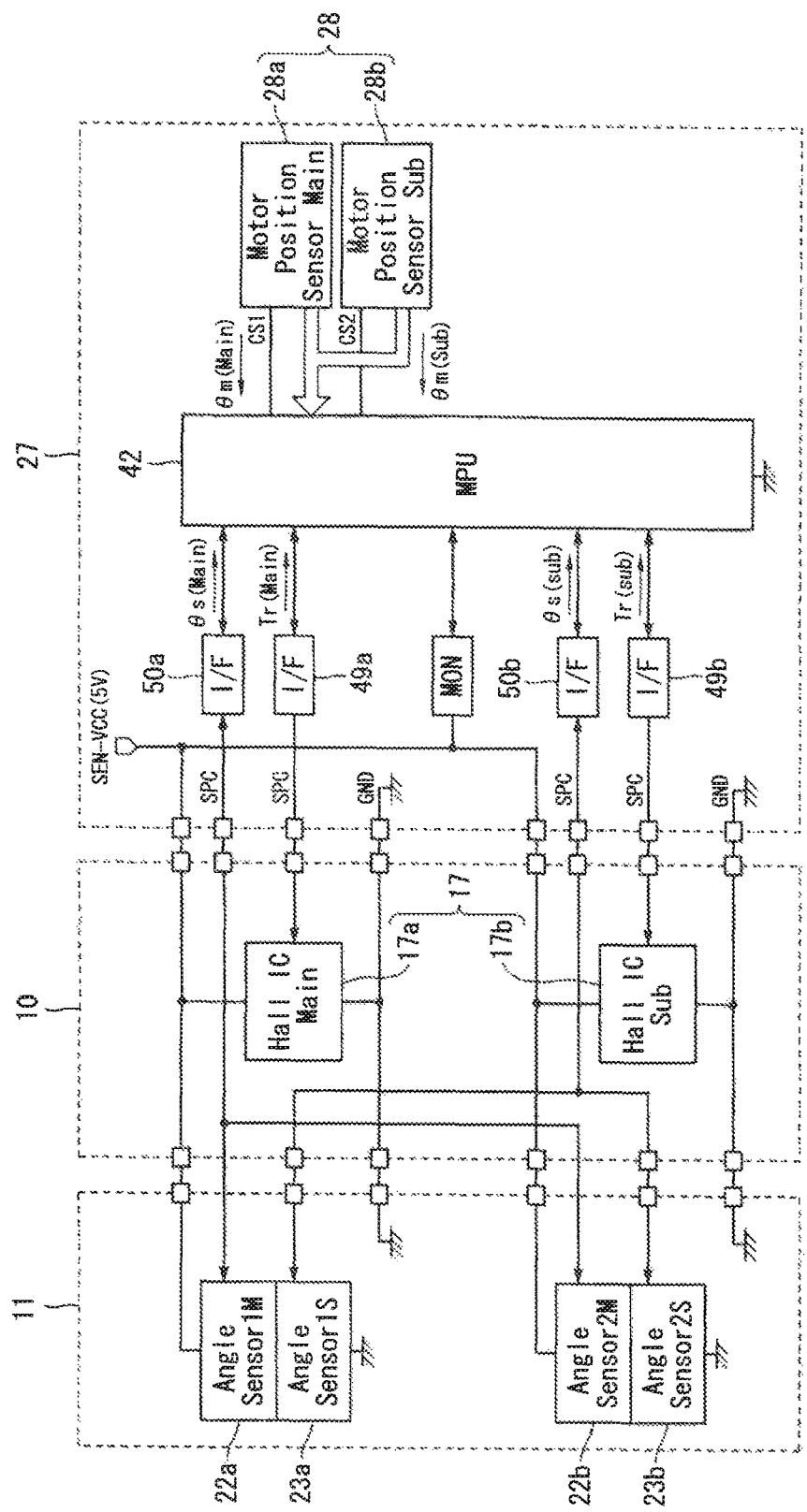
FIG. 7 is a sensor block diagram showing a relationship of connection among the ECU, the torque sensor, the steering angle sensor, and a rotation angle sensor.
Figure 8:
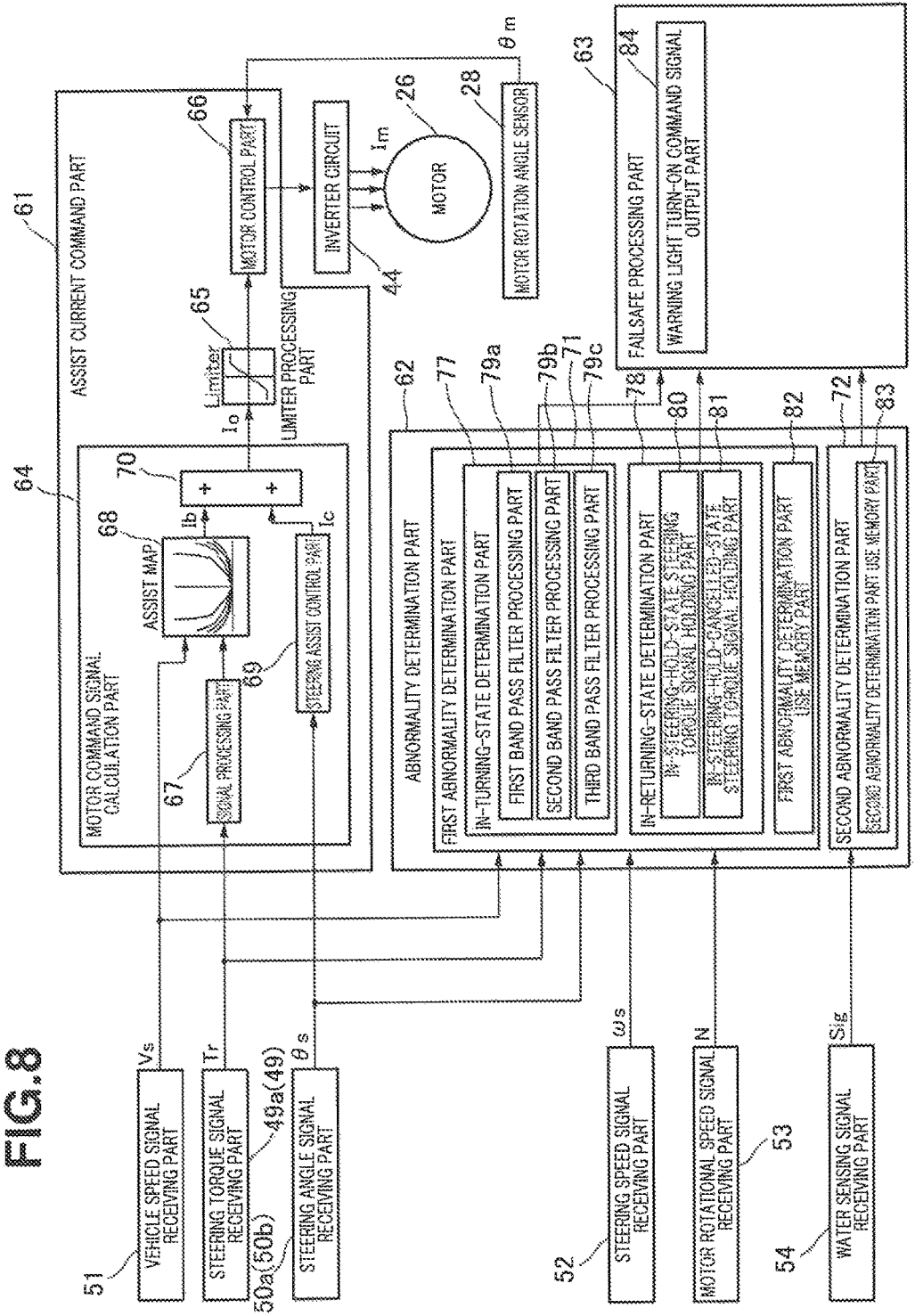
FIG. 8 is a control block diagram showing configuration of a calculating circuit of the ECU according to the first embodiment.

The following describes specific configuration of ECU 27 according to the present embodiment with reference to FIGS. 6 to 8.

FIG. 6 is a block diagram showing configuration of an electrical system of ECU 27. As shown in FIG. 6, ECU 27 includes: a power supply circuit 41 serves as a power supply in ECU 27; an MPU (microprocessor) 42 configured to be started up by power supply from power supply circuit 41, and perform various calculation operations; a pre-driver 43 configured as an integrated circuit (IC) to receive input of a command signal from MPU 42; and an inverter circuit 44 configured to be driven and controlled based on a command signal from pre-driver 43.

When power supply circuit 41 receives supply of electric power from a battery VB in response to on-operation of an ignition switch of the vehicle, power supply circuit 41 supplies the electric power to MPU 42, torque sensor 10, steering angle sensor 11, motor rotation angle sensor 28, water sensor 37, and pre-driver 43, while performing appropriate voltage reduction.

MPU 42 is connected electrically to water sensor 37 and a vehicle speed sensor 45, and is configured to receive input of a water sensing signal Sig from water sensor 37 and a vehicle speed signal Vs from vehicle speed sensor 45, wherein vehicle speed sensor 45 is provided at a differential gear not shown or the like. The water sensing signal Sig is switched in an on-off manner in response to presence and absence of detection of water by water sensor 37, and is set to "0" and inputted to MPU 42 when water is not detected, and is set to "1" and inputted to MPU 42 when water is detected.

MPU 42 is also connected electrically to torque sensor 10, steering angle sensor 11, and motor rotation angle sensor 28, and is configured to receive input of main and auxiliary steering torque signals Tr(Main), Tr(Sub) from torque sensor 10, main and auxiliary steering angle signals θs(Main), θs(Sub) from steering angle sensor 11, main and auxiliary motor rotation angle signals θm(Main), θm(Sub) from motor rotation angle sensor 28. When receiving the main and auxiliary signals of each quantity, MPU 42 uses one of the main and auxiliary signals of each quantity as steering torque signal Tr, steering angle signal θs, and motor rotation angle signal θm for the calculation operations (see FIG. 8).

Specific relationship of connection of torque sensor 10, steering angle sensor 11, and motor rotation angle sensor 28 with respect to MPU 42 is described below.

When receiving a command signal from pre-driver 43, the inverter circuit 44 convers the electric power from battery VB from direct current to alternating current and supply the same to electric motor 26 in accordance with the command signal. A failsafe circuit 56 is disposed between battery VB and inverter circuit 44, and is configured to shut off the electric power sent from battery VB to inverter circuit 44, based on commanding of MPU 42, when a failure or the like occurs in the power steering device.

A motor current sensing part 57 is disposed at a downstream side of inverter circuit 44, and is configured to sense an actual motor current Im that is an actual current flowing through the electric motor 26. The actual motor current Im sensed by motor current sensing part 57 is inputted to a current monitoring circuit 58 provided in ECU 27. Thereafter, actual motor current Im Is applied with high-response filter processing by main and auxiliary current sensing circuits 59a, 59b for motor control in pairs, and is fed back to MPU 42, and is also applied with low-response filter processing by main and auxiliary current sensing circuits 59c, 59d for overcurrent sensing in pairs, and is fed back to MPU 42.

FIG. 7 is a sensor block diagram showing a specific relationship of connection of torque sensor 10, steering angle sensor 11, and motor rotation angle sensor 28 with MPU 42.

As shown in FIG. 7, MPU 42 is connected to main and auxiliary Hall elements 17a, 17b of torque sensor 10 via steering torque signal receiving parts 49a, 49b provided in ECU 27, and is configured to receive input of main and auxiliary steering torque signals Tr(Main), Tr(Sub) sensed by main and auxiliary Hall elements 17a, 17b.

MPU 42 is further connected to main first and second MR elements 22a, 22b of steering angle sensor 11 via a first steering angle signal receiving part 50a provided in ECU 27, and is configured to receive input of steering angle signal θs(Main) calculated based on the angular difference between the first and second rotation angles sensed by main first and second MR elements 22a, 22b, and is also connected to auxiliary first and second MR elements 23a, 23b of steering angle sensor 11 via a second steering angle signal receiving part 50b provided in ECU 27, and is configured to receive input of steering angle signal θs(Sub) calculated based on the angular difference between auxiliary first and second MR elements 23a, 23b.

Moreover, MPU 42 is connected to main and auxiliary angle sensing elements 28a, 28b of motor rotation angle sensor 28, and is configured to receive input of main and auxiliary motor rotation angle signals θm(Main), θm(Sub) from main and auxiliary angle sensing elements 28a, 28b.

FIG. 8 is a control block diagram showing configuration of a calculating circuit of ECU 27.

ECU 27 includes: an assist current command part 61 configured to calculate a motor command signal Io for control of driving of electric motor 26, based on steering torque signal Tr, vehicle speed signal Vs inputted to vehicle speed signal receiving part 51, and steering angle signal θs, and output the motor command signal Io to electric motor 26; an abnormality determination part 62 configured to determine abnormality of the power steering device, based on steering torque signal Tr and others; and a failsafe processing part 63 configured to perform various failsafe operations, based on a result of determination by abnormality determination part 62.

Assist current command part 61 generally includes: a motor command signal calculation part 64 configured to calculate motor command signal Io, based on steering torque signal Tr, vehicle speed signal Vs, and steering angle signal θs; a limiter processing part 65 configured as a command signal limiting part to limit the motor command signal Io calculated by motor command signal calculation part 64 such that the limited motor command signal Io is less than or equal to a predetermined upper limit value; and a motor control part 66 configured to control driving of electric motor 26 by applying a driving current to electric motor 26, based on the motor command signal Io corrected by limiter processing part 65.

Motor command signal calculation part 64 includes a signal processing part 67 configured to process the steering torque signal Tr by noise removal, phase compensation, etc. Motor command signal calculation part 64 calculates a basic signal Ib by using a prepared assist map 68, based on vehicle speed signal Vs and the processed steering torque signal Tr. Motor command signal calculation part 64 further includes: a steering assist control part 69 configured to calculate a correction signal Ic based on steering angle signal θs in parallel; and an adder 70 configured to calculate motor command signal Io by adding the correction signal Ic to basic signal Ib.

Furthermore, motor command signal calculation part 64 is configured to output the motor command signal Io in a range below a motor command signal calculated from vehicle speed signal Vs and steering torque signal Tr when the power steering device is normal, in response to a condition where a second abnormality determination part 72 described below determines that the power steering device is abnormal.

Limiter processing part 65 is configured to control the upper limit value of motor command signal Io variably. For example, when electric motor 26 is overheated, the limiter processing part 65 sets the upper limit value of motor command signal Io lower than in a normal state, during a predetermined failsafe operation.

Motor control part 66 is configured to control driving of electric motor 26, based on motor command signal Io inputted from motor command signal calculation part 64 (limiter processing part 65) and motor rotation angle signal θm inputted from motor rotation angle sensor 28.

Abnormality determination part 62 includes: a first abnormality determination part 71 configured to determine abnormality of the power steering device by a determination logic described below; and second abnormality determination part 72 configured to determine abnormality of the power steering device, based on water sensing signal Sig from water sensor 37.

First abnormality determination part 71 is configured to receive input of steering torque signal Tr sensed by torque sensor 10, steering angle signal θs sensed by steering angle sensor 11, and vehicle speed signal Vs sensed by vehicle speed sensor 45. First abnormality determination part 71 is further configured to receive input of a steering speed signal ωs via a steering speed signal receiving part 52, and a motor rotational speed N via a motor rotational speed signal receiving part 53, wherein steering speed signal ωs is obtained by time-differentiating the steering angle signal θs, and wherein motor rotational speed N is calculated based on motor rotation angle signal θm.

Furthermore, first abnormality determination part 71 includes: an in-turning-state determination part 77 configured to determine abnormality of the power steering device, based on signals such as steering torque signal Tr when steering operation is performed in a turning direction to further turn the steering wheel; and an in-returning-state determination part 78 configured to determine abnormality of the power steering device, based on a change of steering torque signal Tr in a predetermined region including a region when the direction of steering of the steering wheel is shifted from the turning direction to a returning direction.

In-turning-state determination part 77 is configured to perform abnormality determination by using a characteristic that when an abnormality occurs in the power steering device, steering torque signal Tr shows a periodic change only in a predetermined frequency band.

Figure 9A:
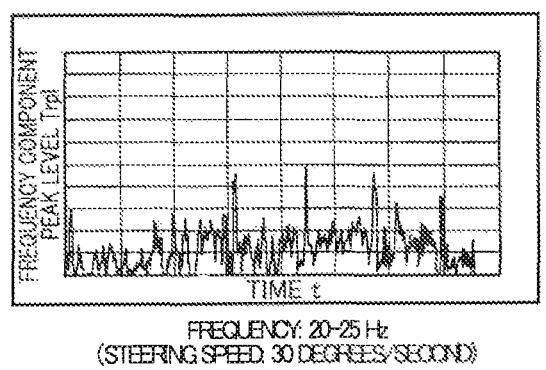
FIG. 9A is a graph showing data obtained by an experiment with a power steering device placed on a stage, wherein the power steering device includes a new ball-screw mechanism.
Figure 9B:
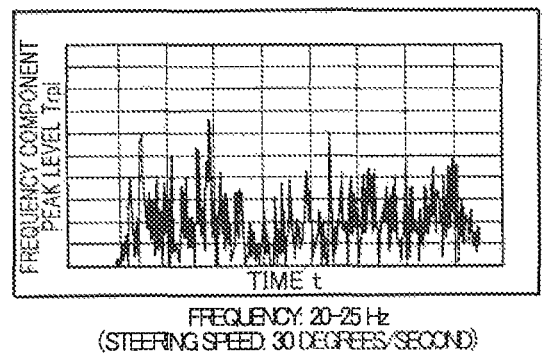
FIG. 9B is a graph showing data obtained by an experiment with a power steering device placed on a stage, wherein the power steering device includes a rusted ball-screw mechanism.

FIGS. 9A and 9B are graphs showing an experimental result when an experiment was performed to demonstrate the characteristic described above.

This experiment was implemented by: placing on respective stages a normal power steering device including a new one of rack bar 7 and a new one of ball screw mechanism 31 (henceforth referred to as normal device), and an abnormal power steering device rusted by immersion in saltwater for nine days (henceforth referred to as abnormal device); performing steering operation at a steering speed of 30 degrees/second; and comparing values of peak level Trpl in a specific frequency band of steering torque signal Tr generated by the steering operation.

The peak level Trpl is obtained by extracting a frequency component of steering torque signal Tr relating to torque fluctuation by band pass filter processing at a specific frequency band, and then averaging peak values of this frequency component. As the value of peak level Trpl increases, steering torque signal Tr contains more frequency component in the specific frequency band.

The experiment was performed with three selected frequency bands of 8-12 Hz, 20-25 Hz, and 40-50 Hz as the specific frequency band.

The experiment has shown that there is little difference in the peak level Trpl of the frequency component between the normal device and the abnormal device for the frequency band of 8-12 Hz and the frequency band of 40-50 Hz of the three frequency bands, whereas the value of peak level Trpl of the abnormal device (see FIG. 9B) is greater than the value of peak level Trpl of the normal device (see FIG. 9A). Conversely, this experimental result shows that it is possible to determine abnormality of the power steering device based on a condition that the value of peak level Trpl of the frequency band of 20-25 Hz is greater than or equal to a predetermined value.

However, this experiment is about comparison between one where the normal device and the abnormal device on the stages, namely, when steering operation is performed under a condition of smooth road, without consideration of rough road running.

In view of the foregoing, another experiment was performed where the peak levels Trpl of frequency components of steering torque signal Tr during smooth road running and during rough road running are compared for frequency bands of steering torque signal Tr.

Figure 10A:
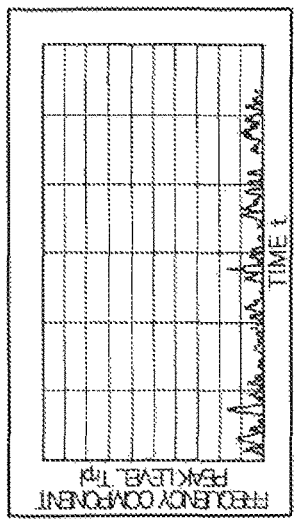
FIGS. 10A to 10C are graphs showing data obtained by an experiment with a paved road.
Figure 10B:
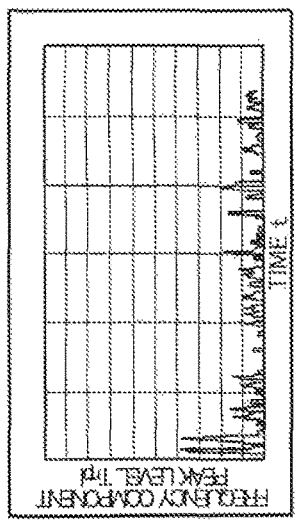
Figure 10C:
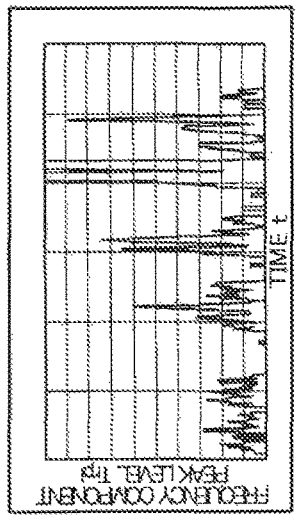

FIGS. 10A to 10C are graphs showing the peak levels Trpl when steering operation is performed on a paved road (smooth road) with the normal device mounted on the vehicle, by plotting for each time t, wherein FIG. 10A relates to the frequency band of 8-12 Hz, FIG. 10B relates to the frequency band of 20-25 Hz, and FIG. 10C relates to the frequency band of 40-50 Hz.

Figure 10D:
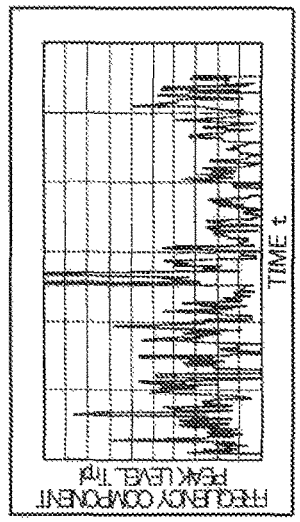
FIGS. 10D to 10F are graphs showing data obtained by an experiment with a gravel road.
Figure 10E:
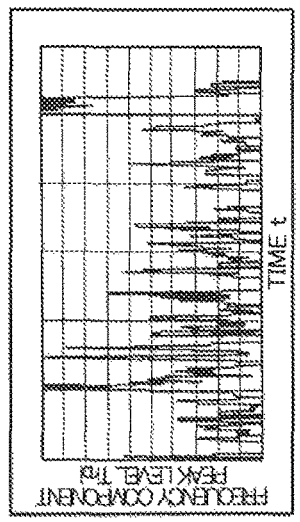
Figure 10F:
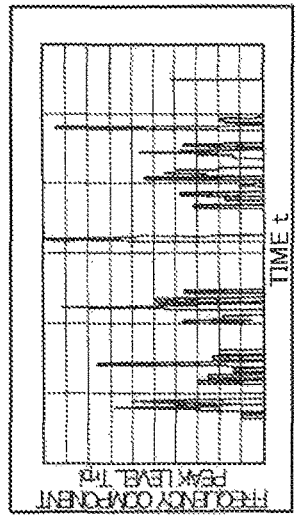

FIGS. 10D to 10F are graphs showing the peak levels Trpl when steering operation is performed on a gravel road (rough road) with the normal device mounted on the vehicle, by plotting for each time t, wherein FIG. 10D relates to the frequency band of 8-12 Hz, FIG. 10E relates to the frequency band of 20-25 Hz, and FIG. 10F relates to the frequency band of 40-50 Hz.

As is clear from FIGS. 10A to 10F, the experiment has shown that when steering operation is performed on a gravel road, the peak level Trpl is made greater by the effect of vibration caused by irregularities of the road surface than on a paved road, for every frequency band. Conversely, this experimental result shows that it is difficult to determine abnormality of the power steering device during rough road running.

In view of the experimental results described above, the in-turning-state determination part 77 according to the present embodiment includes first to third band pass filter processing parts 79a-79c configured to extract frequency components relating to torque fluctuation by band pass filtering for the frequency bands of 8-12 Hz, 20-25 Hz, and 40-50 Hz. In-turning-state determination part 77 determines a road surface based on the peak levels Trpl1-Trpl3 of the frequency bands of 8-12 Hz, 20-25 Hz, and 40-50 Hz extracted by band pass filter processing parts 79a-79c respectively, and thereafter only when determining that the vehicle is running on a smooth road, performs abnormality determination of the power steering device based on changes of the peak levels Trpl1-Trpl3 during steering operation.

In-returning-state determination part 78 is configured to determine abnormality of the power steering device based on dragging of the steering torque during a returning operation in a state where a self-aligning torque is acting, namely, in a state where the steered wheels are returning into a state of straight running in advance to return of the steering wheel. In-returning-state determination part 78 includes: an in-steering-hold-state steering torque signal holding part 80 configured to acquire, as an in-steering-hold-state steering torque signal Ts, the steering torque signal Tr when the steering wheel is turned and held; and an in-steering-hold-cancelled-state steering torque signal holding part 81 configured to acquire, as an in-steering-hold-cancelled-state steering torque signal Td, the steering torque signal Tr immediately after the steering wheel is shifted from the held state to a returning state.

In-returning-state determination part 78 determines that some foreign matter drags the steering wheel when the steering wheel is returned and an abnormality occurs in the power steering device, if the absolute value of a difference $\Delta Tt$ described below is greater than or equal to an abnormality determination threshold valve Tx, wherein the difference $\Delta Tt$ is obtained by subtracting the absolute value of in-steering-hold-cancelled-state steering torque signal Td from the absolute value of in-steering-hold-state steering torque signal Ts.

Second abnormality determination part 72 is configured to determine that the power steering device is normal, when water sensing signal Sig inputted through water sensing signal receiving part 54 has the value of "0", and determine that the power steering device is abnormal, when water sensing signal Sig has the value of "1".

Abnormality determination part 62 includes: a first abnormality determination part use memory part 82 configured to memorize an event that first abnormality determination part 71 determines that the power steering device is abnormal; and a second abnormality determination part use memory part 83 configured to memorize an event that second abnormality determination part 72 determines that the power steering device is abnormal.

First abnormality determination part use memory part 82 is configured to memorize an abnormality sensing counter Cntr described below, whereas second abnormality determination part use memory part 83 is configured to memorize an event that water sensor 37 senses water when the event occurs, and memorize a time period when second abnormality determination part 72 continues to determine that the power steering device is abnormal.

First abnormality determination part use memory part 82 and second abnormality determination part use memory part 83 are independent from each other such that for example, even when second abnormality determination part use memory part 83 as a first one of the memory parts becomes abnormal, only second abnormality determination part use memory part 83 is reset (memorized information is cleared), and the information memorized in first abnormality determination part use memory part 82 as a second one of the memory parts is not cleared.

Failsafe processing part 63 includes a warning light turn-on command signal output part 84. Warning light turn-on command signal output part 84 is configured to output a command signal to turn on a warning light not shown provided on an instrument panel of the vehicle, and thereby warn a driver, when abnormality of the power steering device is determined by at least one of in-turning-state determination part 77 and in-returning-state determination part 78 of first abnormality determination part 71, and second abnormality determination part 72.

Figure 11:
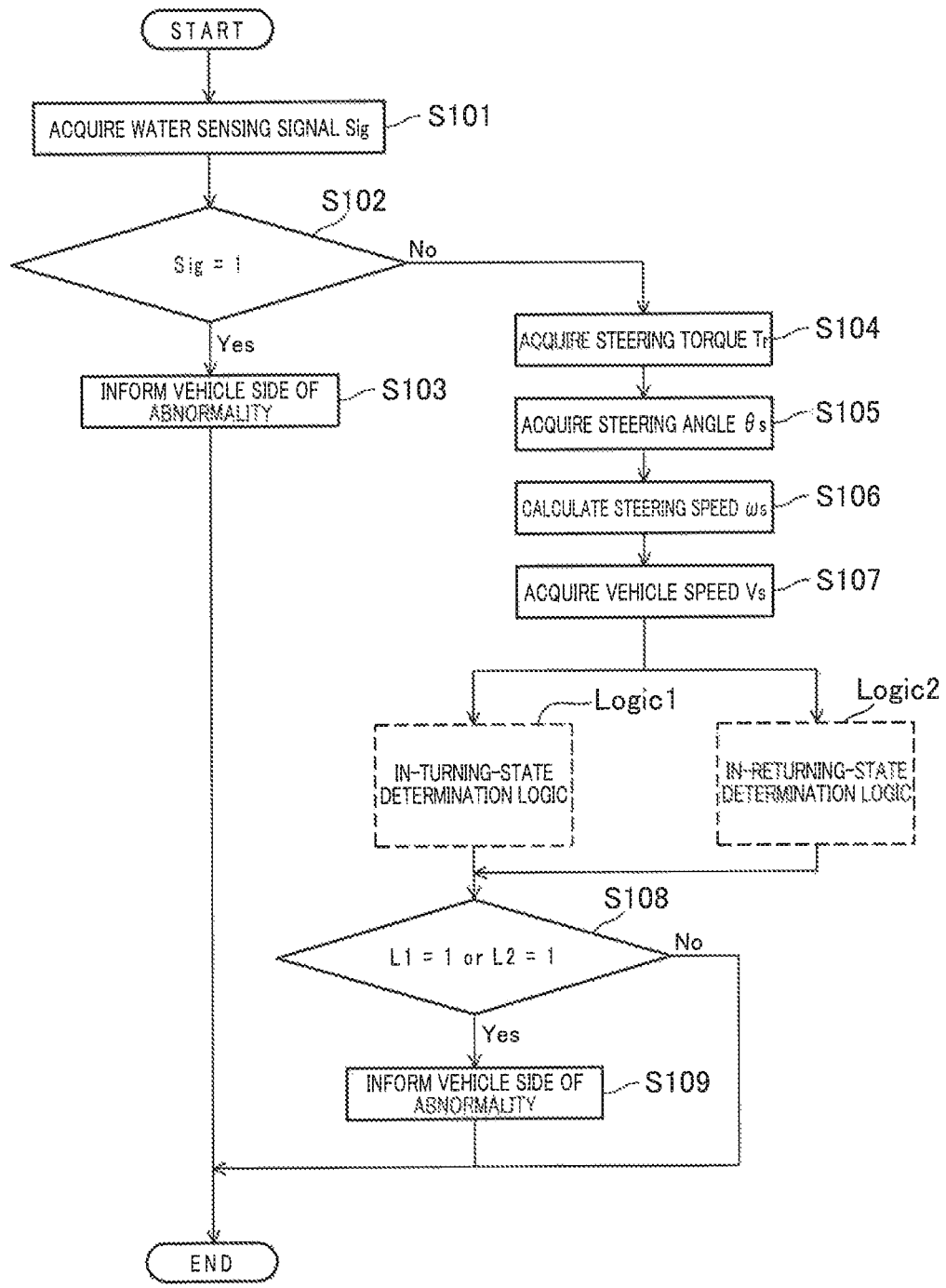
FIG. 11 is a flow chart showing an abnormality determination processing control of the power steering device according to the first embodiment.
Figure 12:
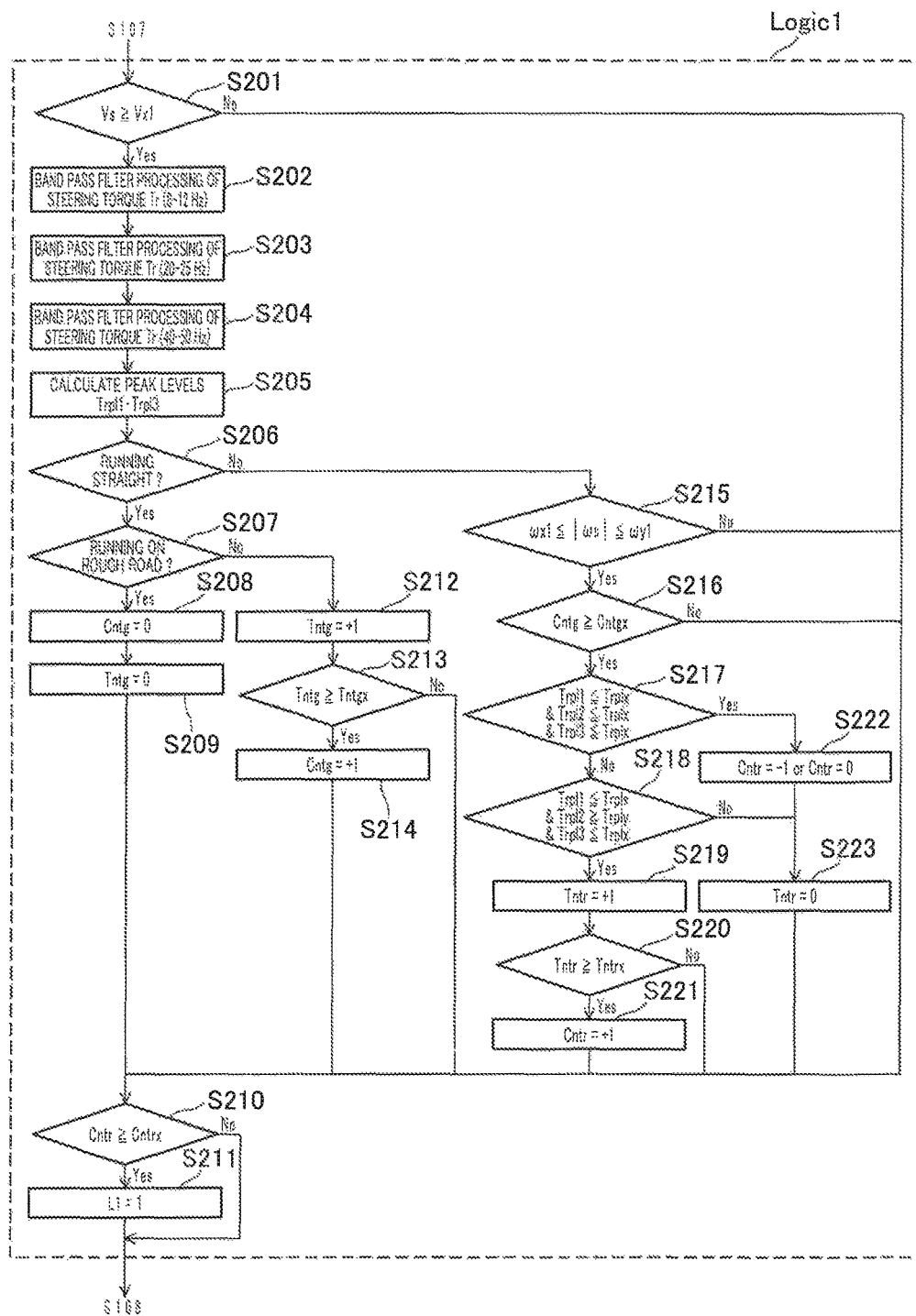
FIG. 12 is a flow chart showing details of an in-turning-state determination logic in FIG. 11.
Figure 13:
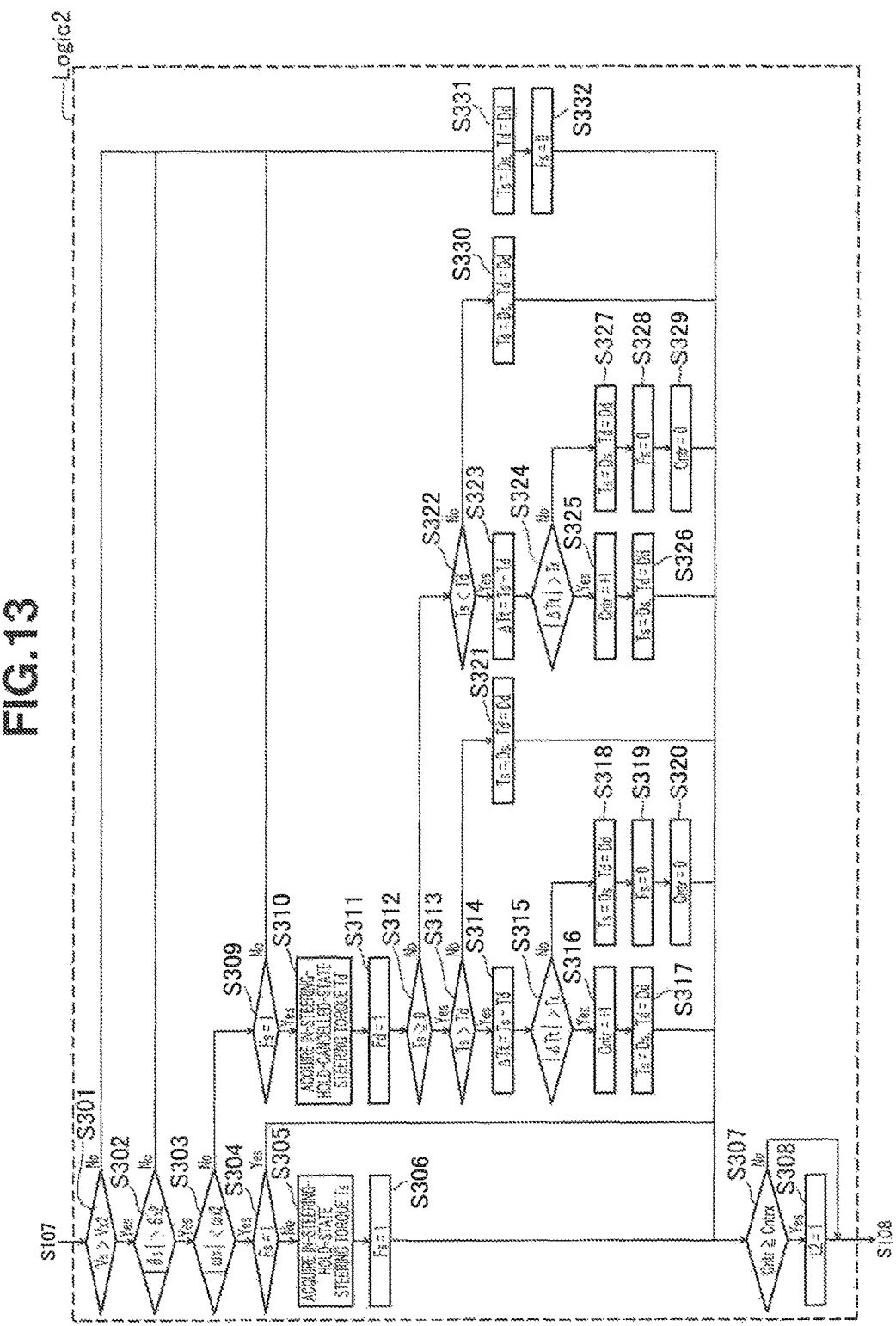
FIG. 13 is a flow chart showing details of an in-returning-state determination logic in FIG. 11.

The following describes a specific process of abnormality determination of ECU 27 about the power steering device according to the present embodiment with reference to FIGS. 11 to 13.

In the following description, steering torque signal Tr, steering angle signal θs, and steering speed signal ωs are set to have positive values when the steering wheel is turned rightward, and have negative values when the steering wheel is turned leftward.

As shown in FIG. 11, ECU 27 acquires data of water sensing signal Sig (Step S101); determines whether or not water sensing signal Sig has the value of "1", namely, whether or not abnormality of the power steering device is detected by water sensor 37 (Step S102); In case of YES, informs the vehicle side of the abnormality, namely, warns a driver by turn-on of the warning light on the instrument panel of the vehicle (Step S103), and terminates the present program.

On the other hand, in case of NO at Step S102, ECU 27 acquires steering torque signal Tr sensed by torque sensor 10 (Step S104); and further acquires steering angle signal θs sensed by steering angle sensor 11 (Step S105). Subsequently, ECU 27 calculates steering speed signal ωs by time-differentiating the steering angle signal θs acquired at Step S105 (Step S106); and acquires vehicle speed signal Vs sensed by vehicle speed sensor 45 (Step S107). Thereafter, ECU 27 proceeds to an in-turning-state determination logic Logic1 (see FIG. 12) and an in-returning-state determination logic Logic2 (see FIG. 13).

As shown in FIG. 12, in the in-turning-state determination logic Logic1, ECU 27 determines whether or not vehicle speed signal Vs is greater than or equal to a predetermined value Vx1 (15 km/h in the present embodiment) (Step S201); and in case of NO, ECU 27 determines whether or not abnormality sensing counter Cntr described below is greater than or equal to a predetermined value Cntrx ("5" in the present embodiment) (Step S210). In case of YES at Step S210, ECU 27 confirms the occurrence of an abnormality in the power steering device, and sets an in-turning-state determination logic abnormality confirmation flag L1 (Step S211), and thereafter proceeds to Step S108 shown in FIG. 11 and described below. On the other hand, in case of NO, ECU 27 assumes that no abnormality of the power steering device is detected in the in-turning-state determination logic Logic1, and proceeds to Step S108.

In case of YES at Step S201 (vehicle speed signal Vs is greater than or equal to 15 km/h), ECU 27 applies band pass filter processing to steering torque signal Tr about the frequency band of 8-12 Hz, the frequency band of 20-25 Hz, and the frequency band of 40-50 Hz (Steps S202 to S204); and calculates peak level Trpl of the frequency component of each frequency band (Step S205). Subsequently, ECU 27 calculates whether or not the vehicle is running straight (Step S206). In the present embodiment, when vehicle speed signal Vs is greater than or equal to 15 km/h, ECU 27 determines that the vehicle is running straight, in response to a condition that steering torque signal Tr Is less than a predetermined value Tx1 (1 Nm in the present embodiment), steering angle signal θs is less than a predetermined value θx1 (30 degrees in the present embodiment), and steering speed signal ωs is less than a predetermined value ωx1 (5 degrees/second in the present embodiment).

In case of YES at Step S206, ECU 27 determines whether or not the vehicle is running on a rough road (Step S207). In the present embodiment, when vehicle speed signal Vs is greater than or equal to 15 km/h, ECU 27 determines that the vehicle is running on a rough road, in response to a condition that at least one of peak levels Trpl1-Trpl3 of the frequency components of the three frequency bands of 8-12 Hz, 20-25 Hz, and 40-50 Hz is greater than or equal to a predetermined value Trplx (0.5 Nm in the present embodiment).

In case of YES at Step S207, ECU 27 clears a smooth counter Cntg described below (Step S208); clears a smooth road running timer Tntg described below (Step S209); and proceeds to Step S210. On the other hand, in case of NO (the vehicle is running on a smooth road), ECU 27 increments smooth road running timer Tntg (Step S212), and thereafter determines whether or not smooth road running timer Tntg is greater than or equal to a predetermined value Tntgx (2 seconds in the present embodiment) (Step S213). In case of NO at Step S213, ECU 27 proceeds directly to Step S210. On the other hand, in case of YES at Step S213, ECU 27 increments smooth road counter Cntg (Step S214), and thereafter proceeds to Step S210.

In case of NO at Step S206 (steering operation is being performed), ECU 27 determines whether or not the absolute value of steering speed signal ωs is greater than or equal to the predetermined value ωx1 (30 degrees), and less than or equal to a predetermined value ωy1 (90 degrees in the present embodiment) (Step S215). In case of NO at Step S215, ECU 27 proceeds to Step S210. On the other hand, in case of YES, ECU 27 determines whether or not smooth road counter Cntg is greater than or equal to a predetermined value Cntgx ("1" In the present embodiment) (Step S216). In case of NO at Step S216, ECU 27 proceeds to Step S210. In case of YES at Step S216, ECU 27 proceeds to Step S217.

At Step S217, ECU 27 determines whether or not all of peak levels Trpl1-Trpl3 are less than or equal to predetermined value Trplx (0.5 Nm in the present embodiment). In case of YES at Step S217, ECU 27 decrements or clears abnormality sensing counter Cntr (Step S222); clears abnormality sensing timer Tntr (Step S223); and thereafter proceeds to Step S210. On the other hand, in case of NO, ECU 27 determines whether or not peak levels Trpl1, Trpl3 of 8-12 Hz and 40-50 Hz are less than or equal to predetermined value Trplx (0.5 Nm) and peak level Trpl2 of 20-25 Hz is greater than or equal to an abnormality determination threshold value Trply (0.8 Nm in the present embodiment) (Step S218).

In case of NO at Step S218, ECU 27 clears abnormality sensing timer Tntr (Step S223), and proceeds to Step S210. On the other hand, in case of YES at Step S218, ECU 27 increments abnormality sensing timer Tntr (Step S219), and determines whether or not abnormality sensing timer Tntr is greater than or equal to a predetermined value Tntrx (0.5 second in the present embodiment) (Step S220). In case of NO at Step S220, ECU 27 proceeds directly to Step S210. On the other hand, in case of YES, ECU 27 increments abnormality sensing counter Cntr (Step S221), and thereafter proceeds to Step S210.

In the in-returning-state determination logic Logic2 shown in FIG. 13, ECU 27 first determines whether or not vehicle speed signal Vs is greater than a predetermined value Vx2 (15 km/h in the present embodiment) (Step S301); in case of NO, resets an in-steering-hold-state steering torque signal Ts described below to a default value Ds ("0" in the present embodiment), and resets an in-steering-hold-cancelled-state steering torque signal Td to a default value Dd ("0" in the present embodiment) (Step S331); rests an in-steering-hold-state steering torque acquirement flag Fs described below (Step S332); and thereafter determines whether or not abnormality sensing counter Cntr is greater than or equal to predetermined value Cntrx (Step S307). In case of YES at Step S307, ECU 27 confirms the occurrence of an abnormality of the power steering device, and sets the in-returning-state determination logic abnormality confirmation flag L2 (Step S308), and thereafter proceeds to Step S108 shown in FIG. 11 and described below. On the other hand, in case of NO, ECU 27 assumes that no abnormality of the power steering device is detected in the in-returning-state determination logic Logic2, and proceeds to Step S108.

On the other hand, in case of YES at Step S301, ECU 27 determines whether or not the absolute value of steering angle signal θs is greater than a predetermined value θx2 (10 degrees in the present embodiment) (Step S302).

In case of NO at Step S302, ECU 27 resets the in-steering-hold-state steering torque signal Ts and in-steering-hold-cancelled-state steering torque signal Td to default values Ds, Dd (Step S331), and resets the in-steering-hold-state steering torque acquirement flag Fs (Step S332), and thereafter proceeds to Step S307. On the other hand, in case of YES, ECU 27 determines whether or not the absolute value of steering speed signal ωs is less than a predetermined value ωx2 (5 degrees/second in the present embodiment), namely, whether the steering wheel is in held state or in steered state (Step S303).

In case of YES at Step S303 (in steering-hold state), ECU 27 determines whether or not the in-steering-hold-state steering torque acquirement flag Fs is set (Step S304). In case of NO at Step S304, ECU 27 acquires, as the in-steering-hold-state steering torque signal Ts, the steering torque signal Tr at the moment (Step S305); sets the in-steering-hold-state steering torque acquirement flag Fs (Step S306); and thereafter proceeds to Step S307. In case of YES, ECU 27 assumes that the in-steering-hold-state steering torque signal Ts has been already acquired, and proceeds directly to Step S307.

On the other hand, in case of NO at Step S303 (in steered state), ECU 27 determines whether or not the in-steering-hold-state steering torque acquirement flag Fs is set (Step S309), as at Step S304. In case of NO at Step S309, ECU 27 proceeds to Step S331. On the other hand, in case of YES at Step S309, ECU 27 acquires, as the in-steering-hold-cancelled-state steering torque signal Td, the steering torque signal Tr at the moment (Step S310); resets the in-steering-hold-state steering torque acquirement flag Fs (Step S311); and thereafter determines whether or not the in-steering-hold-state steering torque signal Ts is greater than or equal to zero, namely, whether the steering wheel is steered rightward or leftward (Step S312).

In case of YES at Step S312 (rightward steering), ECU 27 determines whether or not the in-steering-hold-state steering torque signal Ts is greater than the in-steering-hold-cancelled-state steering torque signal Td, namely, whether or not the steering wheel is returned from the steering-hold state (Step S313). In case of NO (in state of turning), ECU 27 resets the in-steering-hold-state steering torque signal Ts and in-steering-hold-cancelled-state steering torque signal Td to default values Ds, Dd respectively (Step S321), and thereafter proceeds to Step S307. On the other hand, in case of YES (In state of returning), ECU 27 calculates difference ΔTt by subtracting the in-steering-hold-cancelled-state steering torque signal Td from in-steering-hold-state steering torque signal Ts (Step S314), and thereafter determines whether or not the absolute value of difference ΔTt is greater than abnormality determination threshold valve Tx (Step S315).

In case of YES at Step S315, ECU 27 increments abnormality sensing counter Cntr, because dragging occurs when the steering wheel is returned from the steering-hold state, and it is likely that an abnormality occurs in the power steering device (Step S316). Then, ECU 27 resets the in-steering-hold-state steering torque signal Ts and in-steering-hold-cancelled-state steering torque signal Td to default values Ds, Dd respectively (Step S317), and thereafter proceeds to Step S307.

On the other hand, in case of NO at Step S315, ECU 27 resets the in-steering-hold-state steering torque signal Ts and in-steering-hold-cancelled-state steering torque signal Td to default values Ds, Dd respectively (Step S318); resets the in-steering-hold-state steering torque acquirement flag Fs (Step S319); clears abnormality sensing counter Cntr (Step S320); and thereafter proceeds to Step S307.

In case of NO at Step S312 (leftward steering), ECU 27 determines whether or not the in-steering-hold-cancelled-state steering torque signal Td is greater than the in-steering-hold-state steering torque signal Ts, namely, whether the steering wheel is returned or turned further from the steering-hold state (Step S322). In case of NO at Step S322 (in state of turning), ECU 27 resets the in-steering-hold-state steering torque signal Ts and in-steering-hold-cancelled-state steering torque signal Td to default values Ds, Dd respectively (Step S330), and thereafter proceeds to Step S307. On the other hand, in case of YES (in state of returning), ECU 27 calculates difference ΔTt by subtracting the in-steering-hold-state steering torque signal Ts from the in-steering-hold-cancelled-state steering torque signal Td (Step S324), and thereafter performs abnormality determination based on the value of difference ΔTt. The operations of Steps S324-S329 are the same as Steps S315-S320, and specific description thereof is not repeated here.

At Step S108 shown in FIG. 11, ECU 27 determines whether or not an abnormality is detected by at least one of the in-turning-state determination logic Logic1 and in-re-turning-state determination logic Logic2 (Step S108).

Specifically, at Step S108, ECU 27 determines whether or not the in-turning-state determination logic abnormality confirmation flag L1 or the in-returning-state determination logic abnormality confirmation flag L2 is set. In case of YES, ECU 27 informs the vehicle side of the abnormality, namely, warns a driver by turn-on of the warning light on the instrument panel of the vehicle (Step S109), and terminates the present program. On the other hand, in case of NO, ECU 27 assumes that no abnormality is present in the power steering device, and terminates the present program.

<Effects of Action of First Embodiment>

The power steering device configured as described above is capable of determining abnormality of the power steering device from multiple viewpoints by causing the second abnormality determination part 72 to perform abnormality determination for the power steering device based on sensing of water in housing 3 by water sensor 37, and causing the first abnormality determination part 71 to perform abnormality determination for the power steering device by sensing foreign matter such as sand and dust, which is difficult to sense by water sensor 37, based on steering information.

Moreover, in the present embodiment, first abnormality determination part 71 includes in-turning-state determination part 77 and in-returning-state determination part 78 for determining abnormality of the power steering device based on steering information in different states, namely, in the turning state and in the returning state, so that it is possible to perform suitable abnormality determination for each steering condition.

Furthermore, in the present embodiment, abnormality determination part 62 includes first abnormality determination part use memory part 82 and second abnormality determination part use memory part 83 independent from each other, so that even if an abnormality occurs in a first one of first abnormality determination part use memory part 82 and second abnormality determination part use memory part 83, it is sufficient to reset memorized information of the first one of the memory parts, with no influence to the memorized information of a second one of the memory parts. This makes it possible to cause the second one of the memory parts to perform abnormality determination for the power steering device continuously, without resetting the memorized information of the second one of the memory parts, and thereby quickly achieve abnormality sensing of the power steering device.

When second abnormality determination part 72 determines that the power steering device is abnormal, water enters the inside of housing 3 so that it is likely that as time elapses, rust increases and the load of steering increases. If motor command signal Io is corrected to be larger significantly as the load of steering increases in such a situation, the steering load becomes light, but the value of sensed steering torque signal Tr becomes smaller, so that first abnormality determination part 71 may become unable to perform satisfactory abnormality determination for the power steering device.

In view of the foregoing, in the present embodiment, motor command signal calculation part 64 is configured such that when second abnormality determination part 72 determines that the power steering device is abnormal, the outputted motor command signal Io is prevented from exceeding the value of the motor command signal calculated when the power steering device is normal. This serves to suppress the steering assist force outputted by electric motor 26, and thereby allows steering torque signal Tr, which is sensed by torque sensor 10, to increase, and thereby quickly achieve abnormality sensing of the power steering device by first abnormality determination part 71.

<Second Embodiment>

Figure 14:
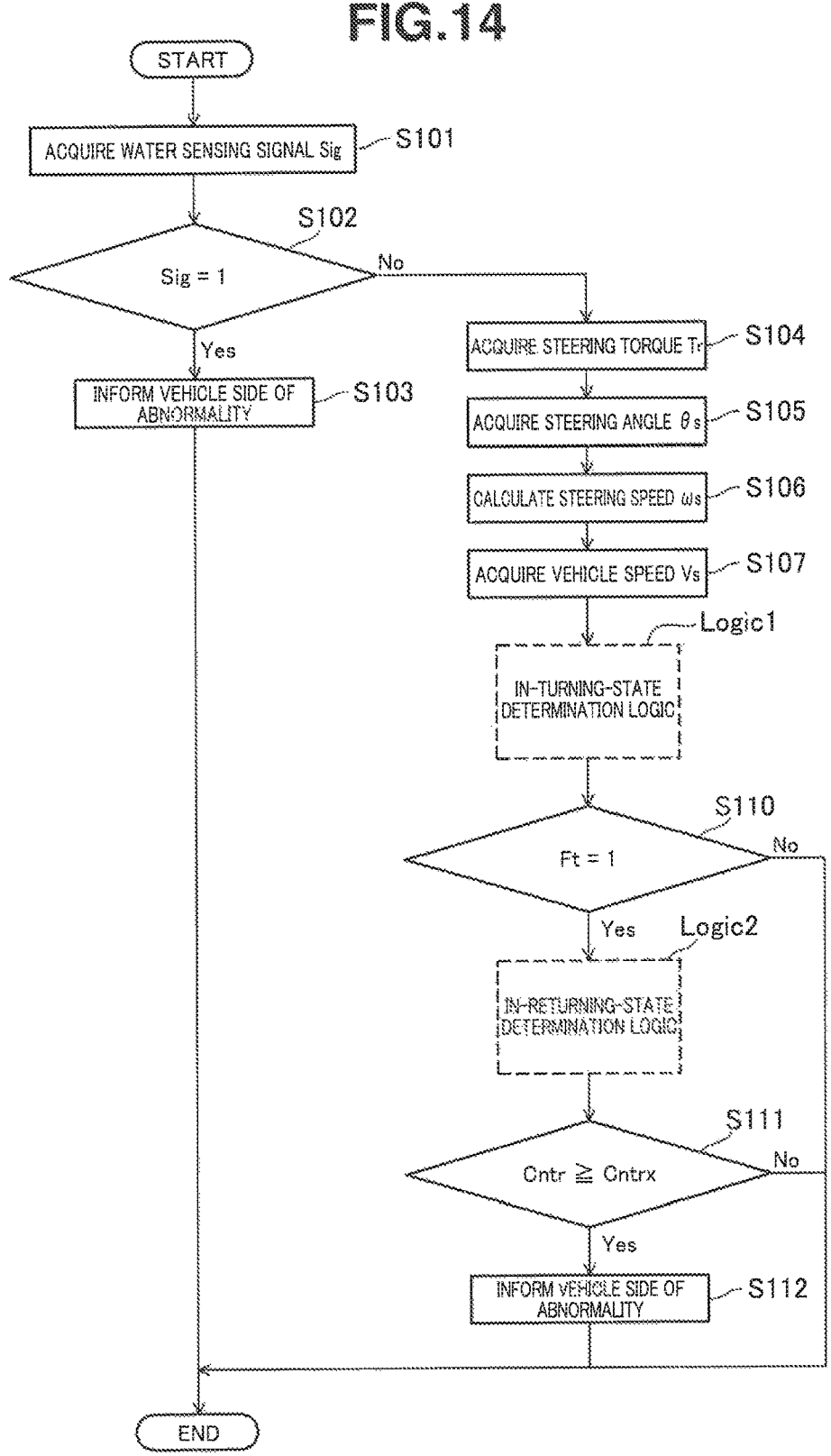
FIG. 14 is a flow chart showing an abnormality determination processing control of a power steering device according to a second embodiment.
Figure 15:
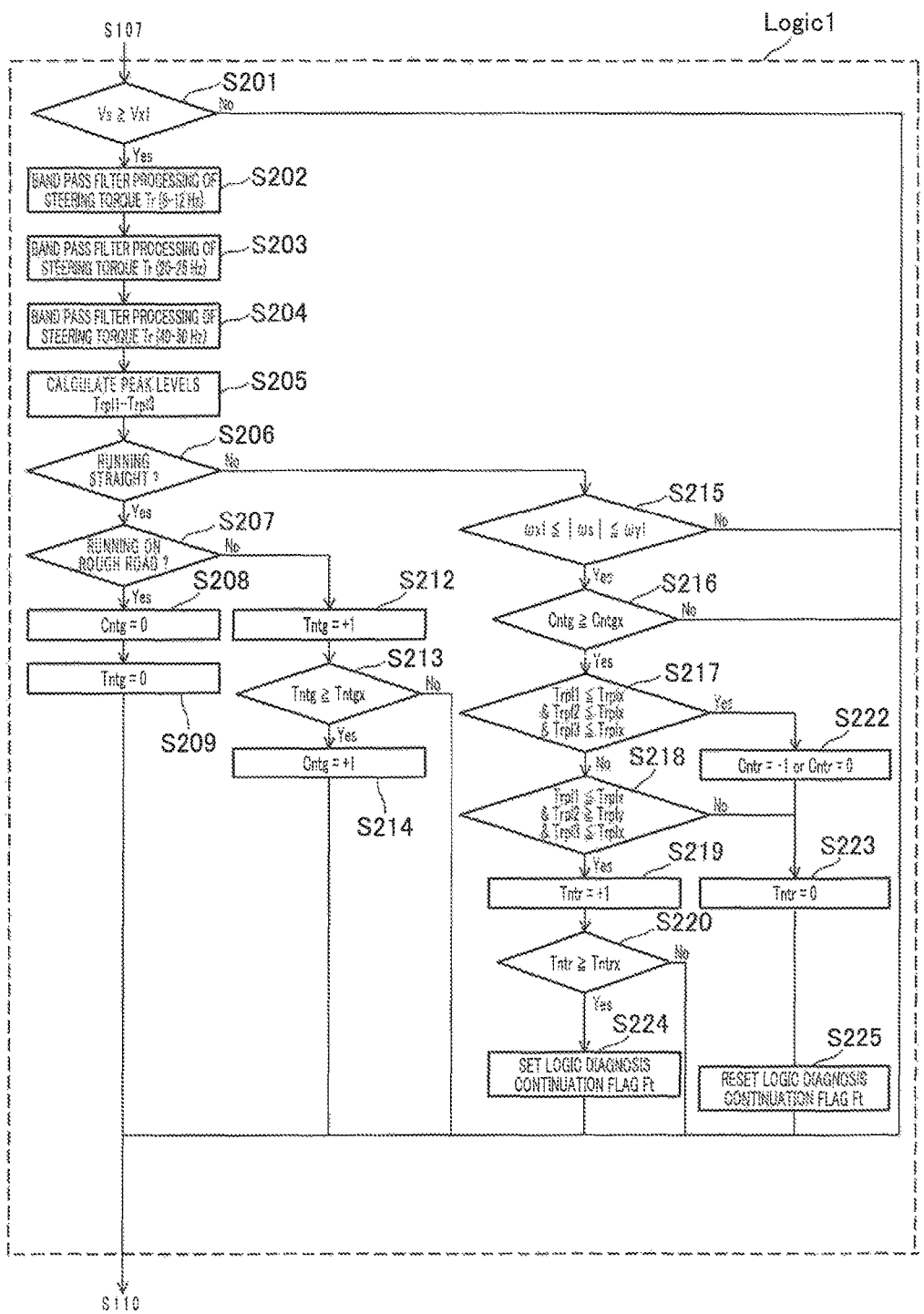
FIG. 15 is a flow chart showing details of an in-turning-state determination logic in FIG. 14.
Figure 16:
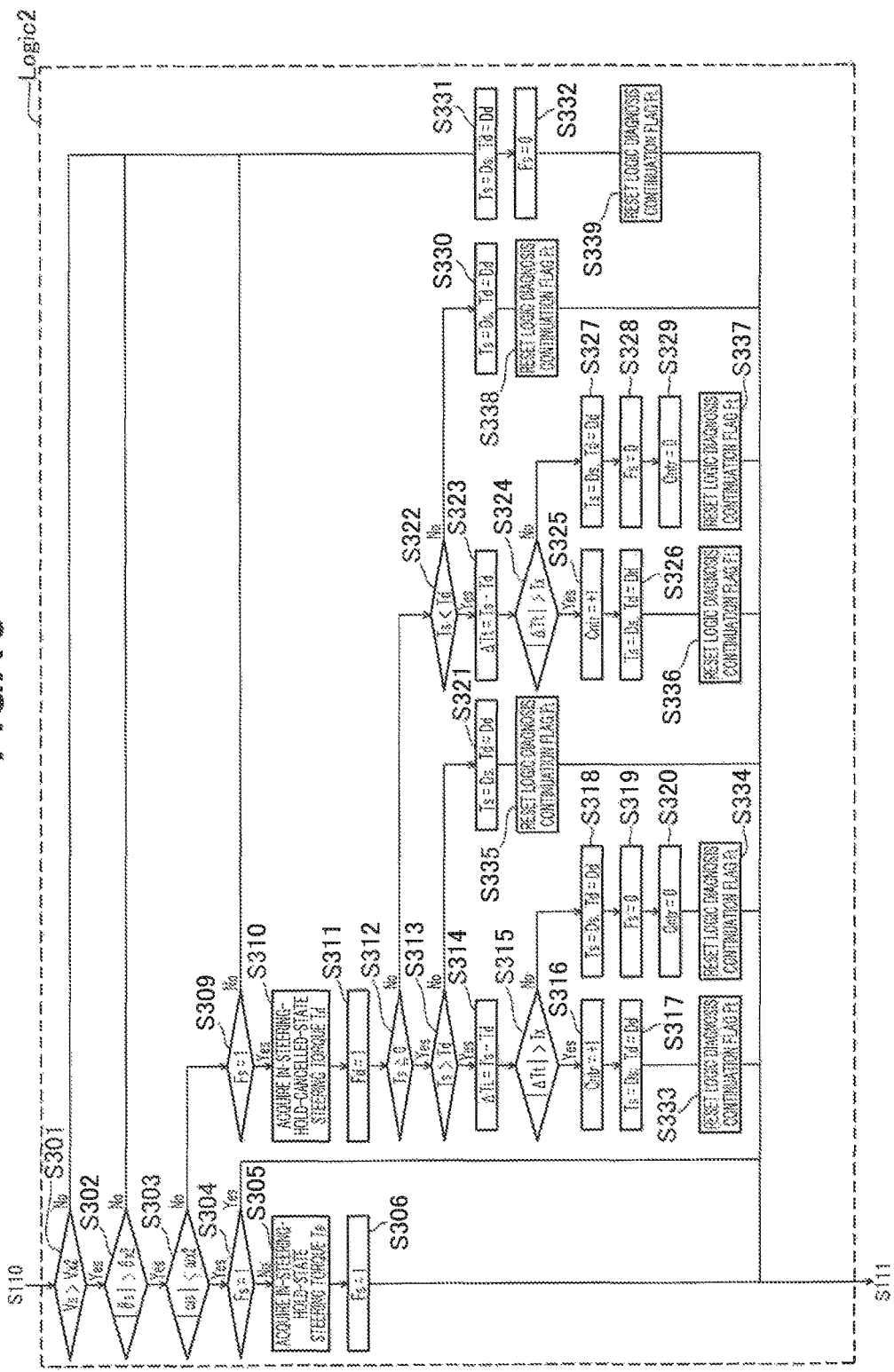
FIG. 16 is a flow chart showing details of an in-returning-state determination logic in FIG. 14.

FIGS. 14 to 16 are flow charts showing an abnormality determination processing control of a power steering device according to a second embodiment of the present invention, wherein the manner of confirming abnormality in each logic Logic1, Logic2 in the flow of abnormality determination processing control of the power steering device according to the first embodiment is modified. Since the second embodiment differs from the first embodiment in only part of the flow, the same symbols are added to the same configuration (operations) as in the first embodiment, and specific description thereof is omitted (also in embodiments described below).

Specifically, as shown in FIG. 14, in the flow of abnormality determination processing control of the power steering device according to the present embodiment, in case of NO at Step S102 where ECU 27 determines whether or not an abnormality of the power steering device is detected by water sensor 37, ECU 27 acquires the various signals (Steps S104 to S107), and thereafter first proceeds to the in-turning-state determination logic Logic1.

As shown in FIG. 15, in the in-turning-state determination logic Logic1 according to the present embodiment, Steps S210 and S211 in the in-turning-state determination logic Logic1 according to the first embodiment are removed. Instead, when determining at Step S220 that abnormality sensing timer Tntr is greater than or equal to the predetermined value, ECU 27 sets a logic diagnosis continuation flag Ft (Step S224), and then proceeds to Step S110. Furthermore, after clearing the abnormality sensing timer Tntr at Step S223, ECU 27 resets the logic diagnosis continuation flag Ft, and proceeds to Step S110.

After completing the process of in-turning-state determination logic Logic1, ECU 27 determines whether or not the logic diagnosis continuation flag Ft Is set (Step S110). In case of NO at Step S110, ECU 27 terminates the present program. On the other hand, in case of YES at Step S110, ECU 27 proceeds to the in-returning-state determination logic Logic2.

As shown in FIG. 16, in the in-returning-state determination logic Logic2 according to the present embodiment, Steps S307 and S308 in the in-returning-state determination logic Logic2 according to the first embodiment are removed. Instead, after the operations of Steps S317, S320, S321, S326, S329, S330, and S332, operations (Steps S333-S339) are added to reset the logic diagnosis continuation flag Ft set at Step S224.

After completing the process of in-returning-state determination logic Logic2, ECU 27 determines whether or not abnormality sensing counter Cntr is greater than or equal to predetermined value Cntrx (Step S111). In case of NO at Step S111, ECU 27 terminates the present program. On the other hand, in case of YES at Step S111, ECU 27 determines that an abnormality occurs in the power steering device, and informs the vehicle side of the abnormality (Step S112), and then terminates the present program.

In this way, in the present embodiment, first abnormality determination part 71 determines that the power steering device is abnormal, when in-turning-state determination part 77 determines that the power steering device is abnormal, based on sensing of a periodic change of steering torque signal Tr, and in-returning-state determination part 78 determines that the power steering device is abnormal, based on a quantity of change of steering torque signal Tr when the steering wheel is returned. This enhances the reliability of abnormality determination of first abnormality determination part 71 about the power steering device, and suppresses incorrect determination.

<Third Embodiment>

Figure 17:
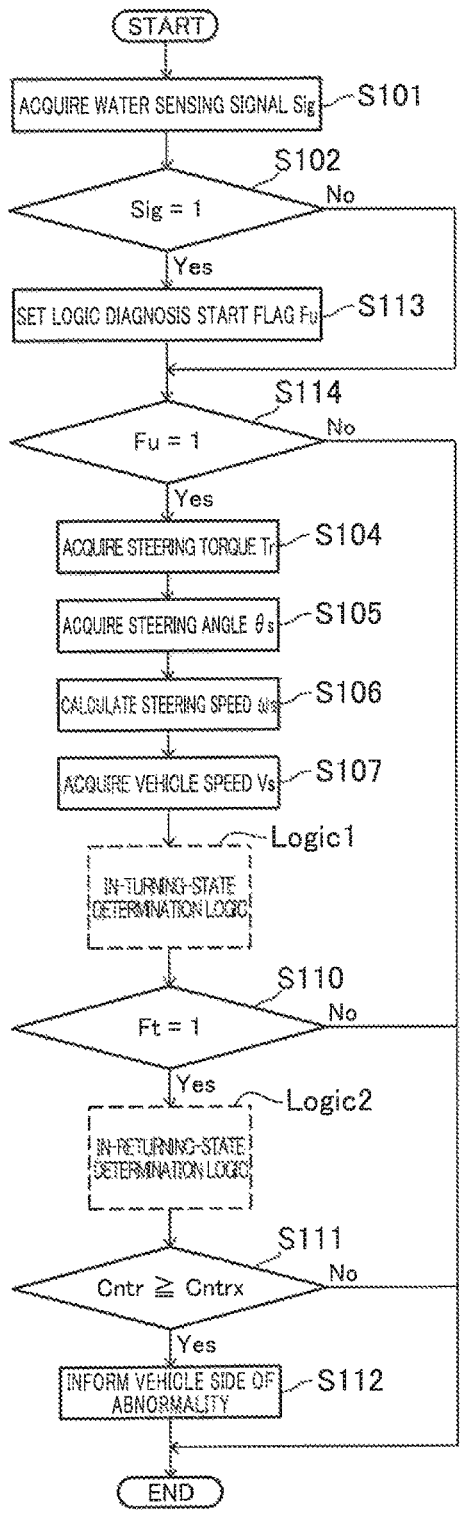
FIG. 17 is a flow chart showing an abnormality determination processing control of a power steering device according to a third embodiment.

FIG. 17 is a flow chart showing an abnormality determination processing control of a power steering device according to a third embodiment of the present invention.

The present embodiment is configured based on the configuration of control according to the second embodiment such that a flag is set after detection of water, and the abnormality determination of the in-turning-state determination logic Logic1 and in-returning-state determination logic Logic2 is performed depending of the presence and absence of the flag.

Specifically, in the flow of abnormality determination control of the power steering device according to the present embodiment, ECU 27 acquires data of water sensing signal Sig (Step S101); determines whether or not water sensing signal Sig has the value of "1", namely, whether or not abnormality of the power steering device is detected by water sensor 37 (Step S102); in case of YES, sets a logic diagnosis start flag Fu (Step S113), and proceeds to Step S114; and in case of NO, proceeds directly to Step S114.

At Step S114, ECU 27 determines whether or not logic diagnosis start flag Fu is set. In case of NO, ECU 27 terminates the present program. On the other hand, in case of YES, ECU 27 proceeds to Step S104.

The following process of Steps S104-S112 is the same as in the second embodiment, and therefore specific description thereof is omitted.

In this way, in the present embodiment, it is determined that the power steering device is abnormal, when second abnormality determination part 72 determines that the power steering device is abnormal, based on detection of water in housing 3, and in-turning-state determination part 77 determines that the power steering device is abnormal, based on sensing of a periodic change of steering torque signal Tr, and in-returning-state determination part 78 determines that the power steering device is abnormal, based on a quantity of change of steering torque signal Tr when the steering wheel is returned. This further enhances the reliability of abnormality determination of first abnormality determination part 71 about the power steering device, and further suppresses incorrect determination. The present embodiment is effective especially in determining an abnormality of the power steering device resulting from the occurrence of rust caused by entrance of water.

<Fourth Embodiment>

Figure 18:
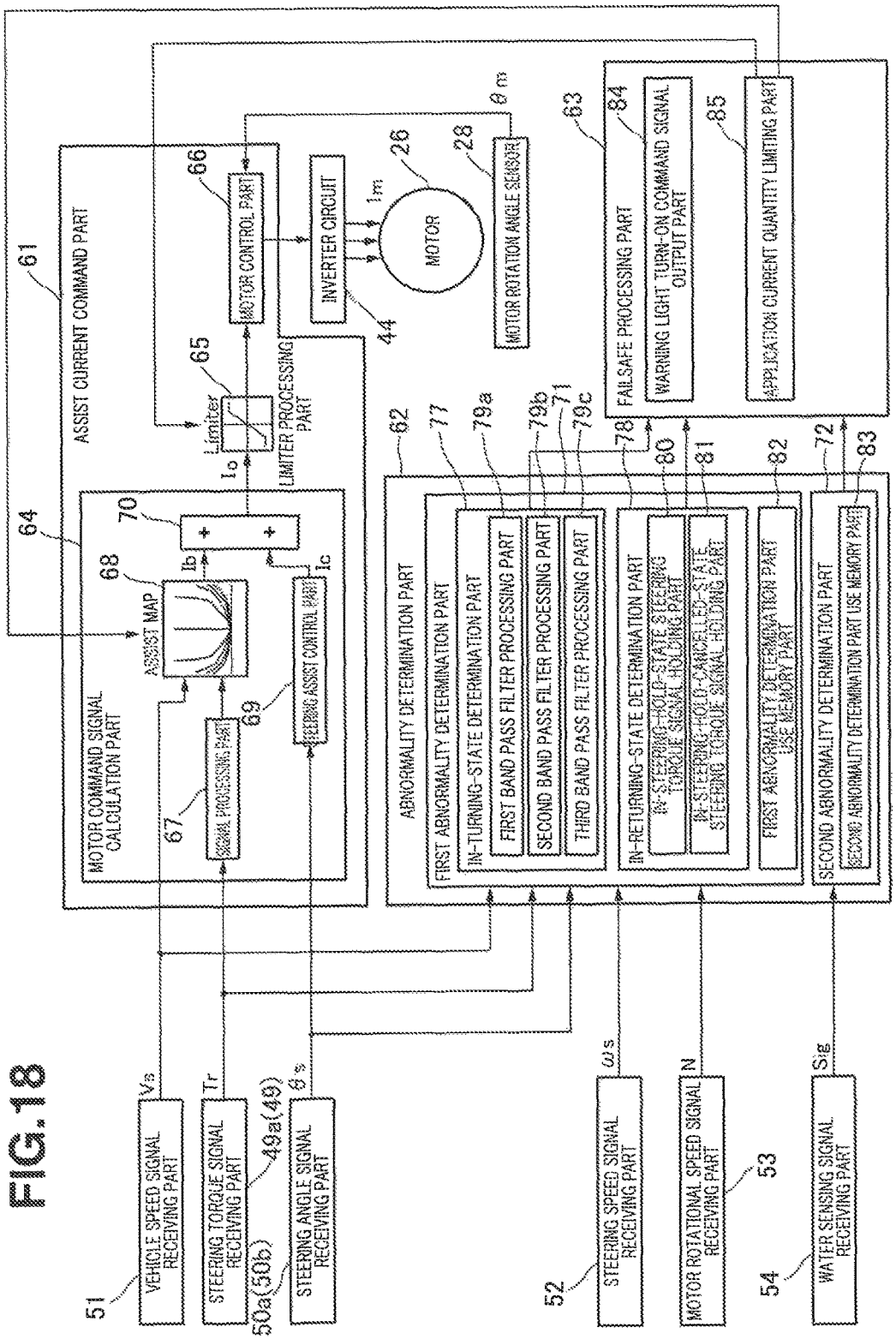
FIG. 18 is a control block diagram showing configuration of a calculating circuit of an ECU according to a fourth embodiment.
Figure 19:
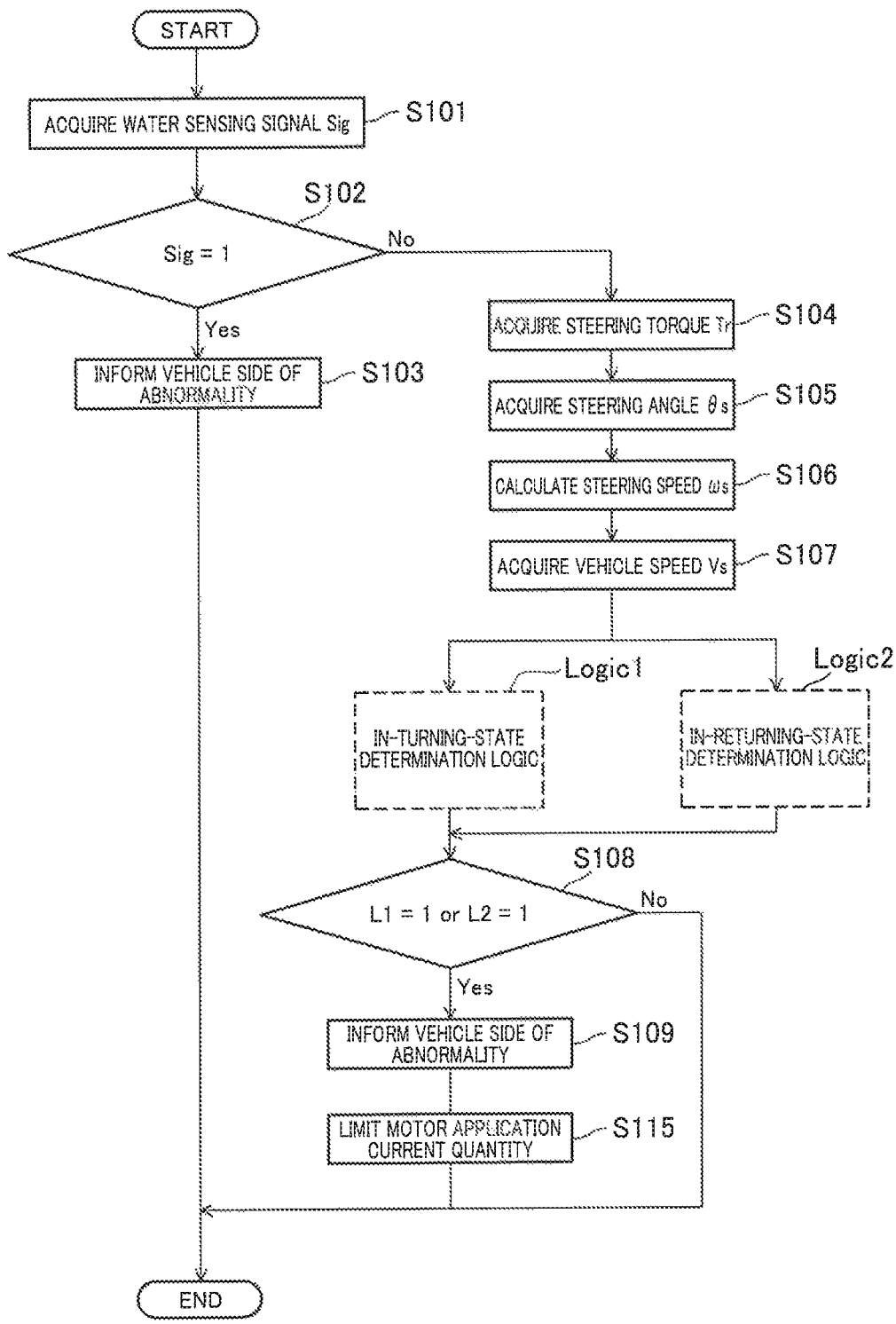
FIG. 19 is a flow chart showing an abnormality determination processing control of a power steering device according to the fourth embodiment.

FIGS. 18 and 19 show a power steering device according to a fourth embodiment of the present invention, which is configured based on the first embodiment such that a function of limiting the steering assist force is added to failsafe processing part 63.

FIG. 18 is a control block diagram showing configuration of a calculating circuit of ECU 27 according to the fourth embodiment of the present invention.

As shown in FIG. 18, failsafe processing part 63 according to the fourth embodiment includes the configuration of the first embodiment, and further includes an application current quantity limiting part 85 configured to limit a motor application current quantity so as to reduce a value of current flowing through the electric motor 26.

Application current quantity limiting part 85 is activated when at least one of the in-turning-state determination part 77 and in-returning-state determination part 78 of first abnormality determination part 71 determines that the power steering device is abnormal; and is configured to limit the motor application current quantity by sending a command signal to limiter processing part 65 so as to further limit the upper limit value of motor command signal Io, or by changing the assist map 68 of motor command signal calculation part 64 so as to calculate the motor command signal Io less than under normal condition.

FIG. 19 is a flow chart showing an abnormality determination processing control of the power steering device according to the fourth embodiment of the present invention. In the present embodiment, in case of YES at Step S108 (determining that the abnormality is confirmed), ECU 27 informs the vehicle side of the abnormality (Step S109), and thereafter limit the motor application current quantity by the means described above (Step S115), and terminates the present program.

The present embodiment is thus configured to: perform steering assist as normal while only informing the vehicle side of the abnormality during the failsafe operation, on a stage of entrance of water where no direct adverse effect occurs to steering operation; and limit the motor application current quantity, in response to detection of a stage where steering operation is adversely affected by rust and others resulting from entrance of water. This serves to put reduction of the steering load and enhancement of the safety in balance.

<Fifth Embodiment>

Figure 20:
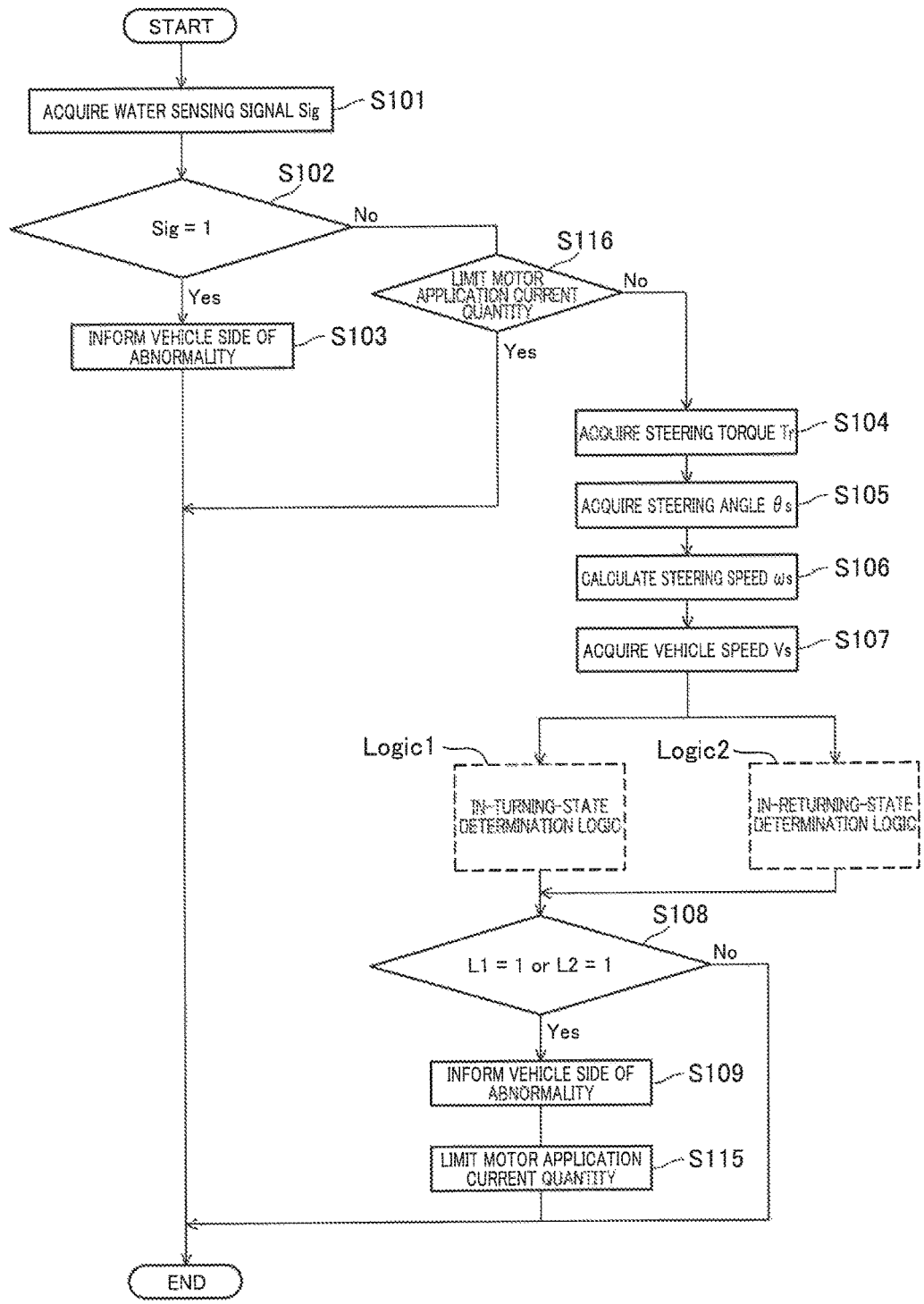
FIG. 20 is a flow chart showing an abnormality determination processing control of a power steering device according to a fifth embodiment.

FIG. 20 shows a power steering device according to a fifth embodiment of the present invention, which is configured based on the fourth embodiment such that the abnormality determination of in-turning-state determination logic Logic1 and in-returning-state determination logic Logic2 is performed based on determination of the presence and absence of the limiter operation after detection of water.

FIG. 20 is a flow chart showing an abnormality determination processing control of the power steering device according to the fifth embodiment. In the flow according to the present embodiment, in case of NO at Step S102 (when no abnormality is determined based on detection of water), ECU 27 determines whether or not the limitation of motor command signal Io by limiter processing part 65 is active (Step S116).

The determination at Step S116 is implemented by determining whether or not the limitation of motor command signal Io by limiter processing part 65 itself is active, without consideration of the limitation of motor command signal Io by application current quantity limiting part 85 based on the result of determination by first abnormality determination part 71.

In case of NO at Step S116, ECU 27 proceeds to Step S104, and thereafter performs the abnormality determination for the power steering device based on the in-turning-state determination logic Logic1 and in-returning-state determination logic Logic2. In case of YES at Step S116, ECU 27 does not perform the abnormality determination for the power steering device based on the in-turning-state determination logic Logic1 and in-returning-state determination logic Logic2, but terminates the present program.

In general, when the limitation of motor command signal Io Is performed based on a factor such as overheating of electric motor 26, the steering assist force also becomes small so that the steering load becomes large, and the signal Tr of steering torque inputted to the steering wheel becomes large. If the abnormality determination of first abnormality determination part 71 about the power steering device is performed in such a situation, incorrect determination may occur.

In contrast, the present embodiment is configured not to perform the abnormality determination of first abnormality determination part 71 about the power steering device while the limitation of motor command signal Io Is being performed by limiter processing part 65. This serves to suppress incorrect determination of first abnormality determination part 71.

<Sixth Embodiment>

Figure 21:
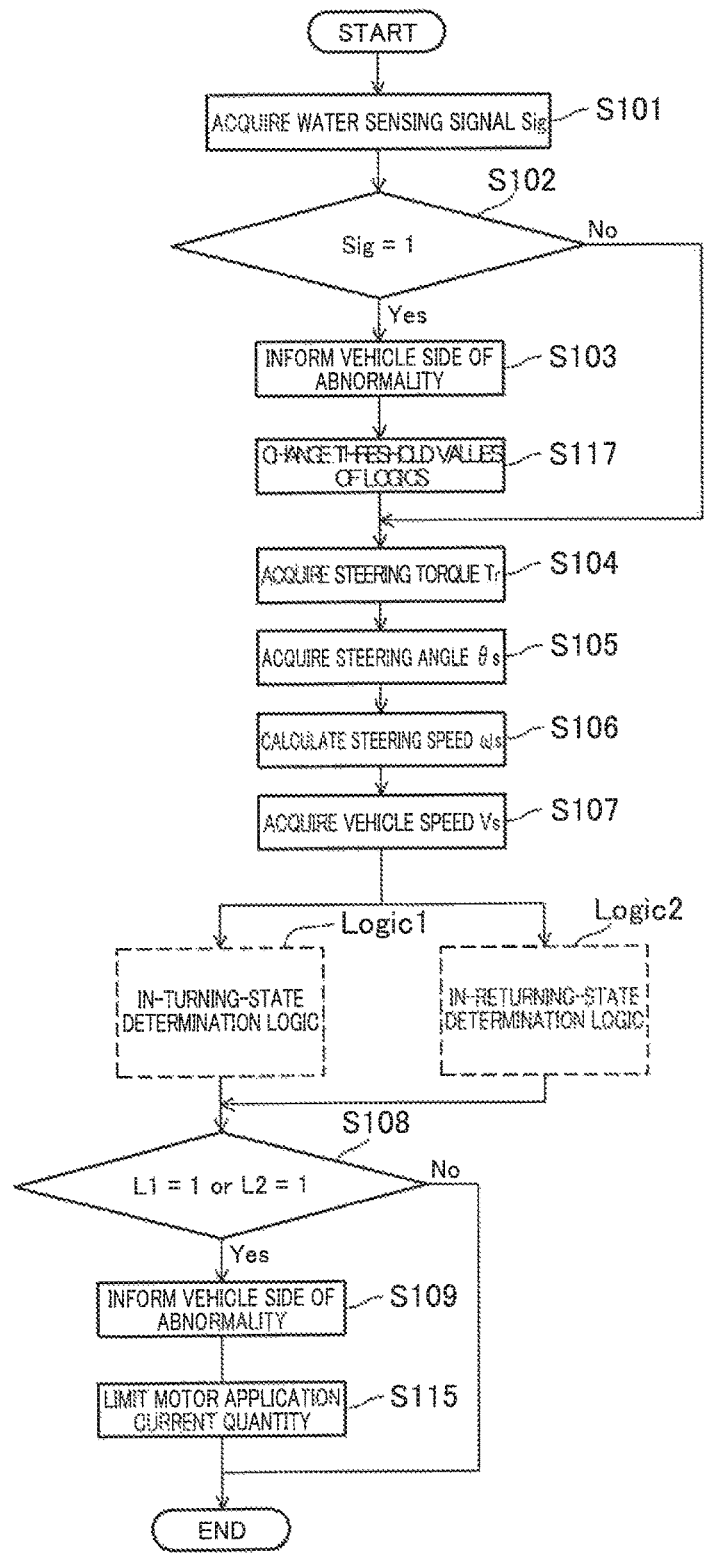
FIG. 21 is a flow chart showing an abnormality determination processing control of a power steering device according to a sixth embodiment.

FIG. 21 shows a power steering device according to a sixth embodiment of the present invention, which is configured based on the control process of abnormality determination of the fourth embodiment such that after abnormality determination based of water detection, the threshold values of in-turning-state determination logic Logic1 and in-returning-state determination logic Logic2 are changed based on the presence and absence of abnormality, and then the abnormality determination of in-turning-state determination logic Logic1 and in-returning-state determination logic Logic2 is performed.

FIG. 21 is a flow chart showing an abnormality determination processing control of the power steering device according to the sixth embodiment.

As shown in FIG. 21, in the present embodiment, both in case of YES and in case of NO at Step S102 where it is determined whether or not an abnormality is detected by water sensor 37, ECU 27 performs the abnormality determination based on the logics.

Furthermore, in the present embodiment, in case of YES at Step S102, namely, when it is determined that water is detected by water sensor 37, ECU 27 informs the vehicle side of the abnormality (Step S103), and performs an operation to reduce determination threshold values for determination of abnormality of the power steering device by first abnormality determination part 71 (Step S117), and thereafter proceeds to Step S104.

The determination thresholds described above are the abnormality determination threshold value Trply in the in-turning-state determination logic Logic1 and the abnormality determination threshold valve Tx in the in-returning-state determination logic Logic2.

The present embodiment is thus configured to perform abnormality determination with reduction of the abnormality determination threshold values Trply, Tx in the logics Logic1, Logic2, when water is detected by water sensor 37, namely, when the occurrence of rust is doubtful. This serves to quickly detect abnormality of the power steering device while suppressing incorrect determination.

<Seventh Embodiment>

Figure 22:
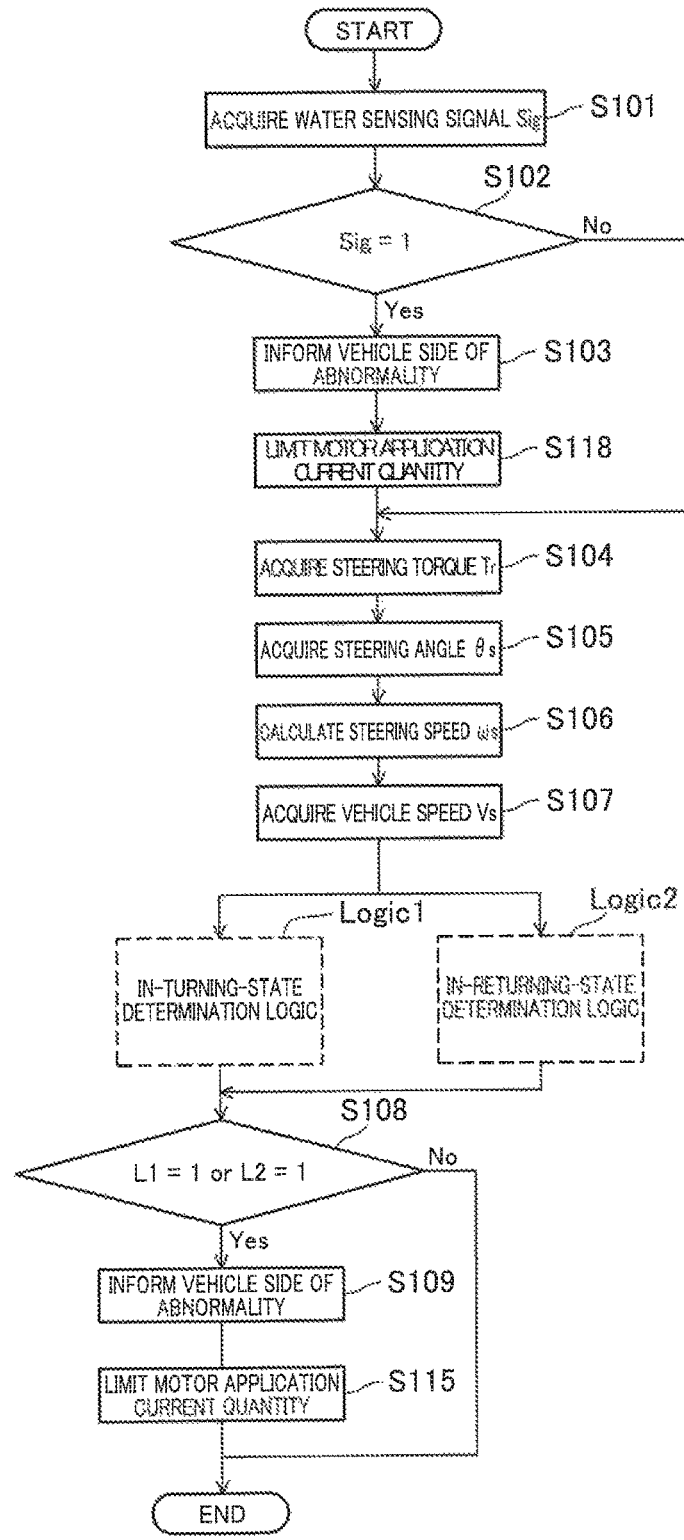
FIG. 22 is a flow chart showing an abnormality determination processing control of a power steering device according to a seventh embodiment.

FIG. 22 is a flow chart showing an abnormality determination processing control of a power steering device according to a seventh embodiment of the present invention, which is configured based on the abnormality determination according to the sixth embodiment such that Step S117 is removed, and Step S118 is added to limit a motor application current quantity.

Application current quantity limiting part 85 according to the present embodiment is configured to set a limiting value of the motor application current quantity greater when abnormality of the power steering device is determined only by first abnormality determination part 71, than when abnormality of the power steering device is determined by both of abnormality determination parts 71, 72.

Specifically, assuming that the motor application current quantity under normal condition is 100%, the limiting value is set such that the motor application current quantity when the abnormality is determined by both of abnormality determination parts 71, 72 is equal to 37.5%, and the motor application current quantity when the abnormality is determined only by first abnormality determination part 71 is equal to 50%.

In the present embodiment where the determination of abnormality of the power steering device is performed by combination of water detection by water sensor 37 and the logics based on steering information, it is possible to estimate a factor of abnormality based on a result of determination.

Specifically, when both of first abnormality determination part 71 and second abnormality determination part 72 determine that the power steering device is abnormal, it can be estimated that the abnormality is caused by the occurrence of rust due to entrance of water into housing 3; and when only first abnormality determination part 71 determines that the power steering device is abnormal, it can be estimated that foreign matter such as sand and dust enters the inside of housing 3.

As the operability of steering when the power steering device is rusted is compared with that when foreign matter such as sand and dust enters the power steering device, the steering load applied to a driver becomes larger in the latter situation. Accordingly, when rust occurs, the steering load is not increased significantly by limiting the motor application current quantity significantly; but when foreign matter such as sand and dust enters the power steering device, the steering load may be increased excessively by limiting the motor application current quantity significantly.

In view of the foregoing, the present embodiment is configured to: basically limit the motor application current quantity significantly when first abnormality determination part 71 determines that the power steering device is abnormal; and if it is conceivable that foreign matter such as sand and dust enters the power steering device, produce a relatively large steering assist force by loosening the limitation of the motor application current quantity. This serves to suppress the steering load from increasing when it is conceivable that foreign matter such as sand and dust enters the power steering device.

<Eighth Embodiment>

FIG. 23 is a flow chart showing an abnormality determination processing control of a power steering device according to an eighth embodiment of the present invention, which is configured based on the abnormality determination control according to the sixth embodiment such that Step S117 is removed, and in case of NO at Step S108, namely, when the abnormality based on the logics is not confirmed, ECU 27 proceeds to Step S119 where ECU 27 determines whether the determination of water detection is correct or incorrect.

Specifically, at Step S119, ECU 27 determines whether or not a predetermined time period has elapsed after second abnormality determination part 72 determines that the power steering device is abnormal, or whether or not stop and start of the vehicle is repeated at a predetermined number of times or more, based on memorized information of second abnormality determination part use memory part 83. In case of NO at Step S119, ECU 27 terminates the present program. On the other hand, in case of YES at Step S119, ECU 27 determines that the water sensor is abnormal (Step S120), and clears the informing the vehicle side of the abnormality (Step S121), and thereafter terminates the present program.

When second abnormality determination part 72 determines that the power steering device is abnormal, it is likely that water enters the inside of housing 3, and the water causes rust, and first abnormality determination part 71 also determines that the power steering device is abnormal.

In a situation where first abnormality determination part 71 does not determine the abnormality of the power steering device even after the predetermined time period has elapsed or stop and start of the vehicle is repeated at the predetermined number of times or more, it can be assumed that an abnormality occurs in second abnormality determination part 72 or the quantity of the water entering the housing 3 is too small to cause rust.

The present embodiment is configured to determine that second abnormality determination part 72 is abnormal in such a situation, and clear the informing the vehicle side of the abnormality, and is thereby capable of suppressing a driver from being warned unnecessarily.

In case of a conventional power steering device where abnormality determination is based only on water detection, even if an abnormality occurs in a water sensor, it is possible that a steering assist force is limited unnecessarily based on a result of determination of the abnormal water sensor.

In contrast, the present embodiment is configured to: determine abnormality of the power steering device based on first abnormality determination part 71, when an abnormality occurs in second abnormality determination part 72; and limit the motor application current quantity by application current quantity limiting part 85 based on the result of the determination. This serves to prevent the steering assist force from being limited unnecessarily based on the determination of the second abnormality determination part 72 in the abnormal state, and thereby enhance the continuity of the steering assist.

The present invention is not limited to the configurations of the embodiments described above. Specific configuration of the present invention may be modified in accordance with device specifications without going out of the substance of the present invention.

For example, the abnormality determination control process of first abnormality determination part 71 about the power steering device is not limited to the configurations of control shown in the present embodiments, but may be configured arbitrarily only if abnormality of the power steering device can be determined based on steering torque signal Tr, motor rotational speed N, or steering speed signal ωs when steering operation is being performed.

The present embodiments are described wherein the in-turning-state determination part 77 applies band pass filtering to steering torque signal Tr, and determines whether or not the component of steering torque signal Tr in the predetermined frequency band has a periodic change, and thereby determines whether the power steering device is abnormal. However, when steering torque signal Tr has a periodic change, motor rotational speed N, and steering speed signal ωs also have periodic changes. Accordingly, motor rotational speed N or steering speed signal ωs may be employed for determination of abnormality of the power steering device by in-turning-state determination part 77.

The power steering devices and the power steering device control devices according to the embodiments described above can be implemented by the following modes, for example.

According to one mode, a power steering device control device for a power steering device, the power steering device including: a steering mechanism configured to transmit rotation of a steering wheel to a steered wheel; an electric motor configured to apply a steering force to the steering mechanism; a transmission mechanism disposed between the steering mechanism and the electric motor, and configured to transmit a torque of the electric motor to the steering mechanism; a housing configured to accommodate the transmission mechanism, the electric motor, and at least part of the steering mechanism; a water sensing element disposed in the housing, and configured to sense water in the housing; and a torque sensor configured to sense a steering torque occurring in the steering mechanism; the power steering device control device includes: a motor command signal calculation part configured to calculate a motor command signal for control of driving of the electric motor, based on the steering torque; a torque signal receiving part configured to receive input of a signal of the steering torque; a motor rotational speed signal receiving part configured to receive input of a signal of rotational speed of the electric motor; a steering speed signal receiving part configured to receive input of a signal of steering speed of the steering wheel; a first abnormality determination part configured to determine that the power steering device is abnormal, based on one of the signals of the steering torque, the rotational speed of the electric motor, and the steering speed when steering operation is being performed; and a second abnormality determination part configured to determine that the power steering device is abnormal, in response to detection of water by the water sensing element.

According to a preferable mode, the power steering device control device is configured such that: the first abnormality determination part includes: an in-turning-state determination part configured to determine whether or not one of the signals of the steering torque, the rotational speed of the electric motor, and the steering speed when steering operation is performed to the steering wheel in a direction of further turn, has a periodic change in a predetermined frequency band; and an in-returning-state determination part configured to sense a change of the steering torque in a predetermined region including a region in which the steering wheel is shifted from the direction of further turn to a direction of return; and the first abnormality determination part is configured to determine that the power steering device is abnormal, based on a result of determination by one of the in-turning-state determination part and the in-returning-state determination part.

According to another preferable mode, the power steering device control device is configured such that the first abnormality determination part is configured to determine that the power steering device is abnormal, in response to a condition that the in-turning-state determination part senses the periodic change and the in-returning-state determination part determines that the change of the steering torque is greater than or equal to a predetermined value.

According to another preferable mode, the power steering device control device further includes: a warning light turn-on command signal output part configured to output a command signal to turn on a warning light of a vehicle in response to determination by the second abnormality determination part that the power steering device is abnormal; and an application current quantity limiting part configured to limit an application current quantity to reduce a value of current flowing through the electric motor, in response to determination by the first abnormality determination part that the power steering device is abnormal.

According to another preferable mode, the power steering device control device further includes a command signal limiting part configured to limit the motor command signal, wherein the first abnormality determination part is further configured to stop determination of abnormality of the power steering device, when the motor command signal is limited by the command signal limiting part.

According to another preferable mode, the power steering device control device is configured such that the first abnormality determination part is further configured to reduce a determination threshold value employed for determining that the power steering device is abnormal, in response to determination by the second abnormality determination part that the power steering device is abnormal.

According to another preferable mode, the power steering device control device further includes: a first abnormality determination part use memory part configured to memorize an event that the first abnormality determination part determines that the power steering device is abnormal; and a second abnormality determination part use memory part configured to memorize an event that the second abnormality determination part determines that the power steering device is abnormal; wherein information memorized in the second abnormality determination part use memory part is cleared without clearance of information memorized in the first abnormality determination part use memory part, in response to occurrence of an abnormality in the second abnormality determination part use memory part.

According to another preferable mode, the power steering device control device is configured such that the motor command signal calculation part is further configured to calculate the motor command signal in a manner to prevent a value of the motor command signal, which is actually outputted to the electric motor, from exceeding a value of the motor command signal that is calculated based on vehicle speed and the steering torque when the power steering device is normal, in response to determination by the second abnormality determination part that the power steering device is abnormal.

According to another preferable mode, the power steering device control device further includes an application current quantity limiting part configured to limit an application current quantity to reduce a value of current flowing through the electric motor, in response to determination by the first abnormality determination part that the power steering device is abnormal, wherein the application current quantity limiting part is configured to limit the application current quantity such that a limiting value of the application current quantity when abnormality of the power steering device is determined only by the first abnormality determination part is greater than that when abnormality of the power steering device is determined by both of the first abnormality determination part and the second abnormality determination part.

According to another preferable mode, the power steering device control device is configured such that it is determined that determination of the second abnormality determination part is incorrect, unless the first abnormality determination part determines that the power steering device is abnormal, even after a predetermined time period elapses or after stop and start of a vehicle is repeated at a predetermined number of times after the second abnormality determination part determines that the power steering device is abnormal.

According to one mode, a power steering device includes: a steering mechanism configured to transmit rotation of a steering wheel to a steered wheel; an electric motor configured to apply a steering force to the steering mechanism; a transmission mechanism disposed between the steering mechanism and the electric motor, and configured to transmit a torque of the electric motor to the steering mechanism; a housing configured to accommodate the transmission mechanism, the electric motor, and at least part of the steering mechanism; a water sensing element disposed in the housing, and configured to sense water in the housing; a torque sensor configured to sense a steering torque occurring in the steering mechanism; and a control device configured to control driving of the electric motor; the control device including: a motor command signal calculation part configured to calculate a motor command signal for control of driving of the electric motor, based on the steering torque; a torque signal receiving part configured to receive input of a signal of the steering torque; a motor rotational speed signal receiving part configured to receive input of a signal of rotational speed of the electric motor; a steering speed signal receiving part configured to receive input of a signal of steering speed of the steering wheel; a first abnormality determination part configured to determine that the power steering device is abnormal, based on one of the signals of the steering torque, the rotational speed of the electric motor, and the steering speed when steering operation is being performed; and a second abnormality determination part configured to determine that the power steering device is abnormal, in response to detection of water by the water sensing element.

According to a preferable mode, the power steering device is configured such that: the first abnormality determination part includes: an in-turning-state determination part configured to determine whether or not one of the signals of the steering torque, the rotational speed of the electric motor, and the steering speed when steering operation is performed to the steering wheel in a direction of further turn, has a periodic change in a predetermined frequency band; and an in-returning-state determination part configured to sense a change of the steering torque in a predetermined region including a region in which the steering wheel is shifted from the direction of further turn to a direction of return; and the first abnormality determination part is configured to determine that the power steering device is abnormal, based on a result of determination by one of the in-turning-state determination part and the in-returning-state determination part.

According to another preferable mode, the power steering device is configured such that the first abnormality determination part is configured to determine that the power steering device is abnormal, in response to a condition that the in-turning-state determination part senses the periodic change and the in-returning-state determination part determines that the change of the steering torque is greater than or equal to a predetermined value.

According to another preferable mode, the power steering device further includes: a warning light turn-on command signal output part configured to output a command signal to turn on a warning light of a vehicle in response to determination by the second abnormality determination part that the power steering device is abnormal; and an application current quantity limiting part configured to limit an application current quantity to reduce a value of current flowing through the electric motor, in response to determination by the first abnormality determination part that the power steering device is abnormal.

According to another preferable mode, the power steering device further includes a command signal limiting part configured to limit the motor command signal, wherein the first abnormality determination part is further configured to stop determination of abnormality of the power steering device, when the motor command signal is limited by the command signal limiting part.

According to another preferable mode, the power steering device is configured such that the first abnormality determination part is further configured to reduce a determination threshold value employed for determining that the power steering device is abnormal, in response to determination by the second abnormality determination part that the power steering device is abnormal.

According to another preferable mode, the power steering device further includes: a first abnormality determination part use memory part configured to memorize an event that the first abnormality determination part determines that the power steering device is abnormal; and a second abnormality determination part use memory part configured to memorize an event that the second abnormality determination part determines that the power steering device is abnormal; wherein information memorized in the second abnormality determination part use memory part is cleared without clearance of information memorized in the first abnormality determination part use memory part, in response to occurrence of an abnormality in the second abnormality determination part use memory part.

According to another preferable mode, the power steering device is configured such that the motor command signal calculation part is further configured to calculate the motor command signal in a manner to prevent a value of the motor command signal, which is actually outputted to the electric motor, from exceeding a value of the motor command signal that is calculated based on vehicle speed and the steering torque when the power steering device is normal, in response to determination by the second abnormality determination part that the power steering device is abnormal.

According to another preferable mode, the power steering device further includes an application current quantity limiting part configured to limit an application current quantity to reduce a value of current flowing through the electric motor, in response to determination by the first abnormality determination part that the power steering device is abnormal, wherein the application current quantity limiting part is configured to limit the application current quantity such that a limiting value of the application current quantity when abnormality of the power steering device is determined only by the first abnormality determination part is greater than that when abnormality of the power steering device is determined by both of the first abnormality determination part and the second abnormality determination part.

According to another preferable mode, the power steering device is configured such that it is determined that determination of the second abnormality determination part is incorrect, unless the first abnormality determination part determines that the power steering device is abnormal, even after a predetermined time period elapses or after stop and start of a vehicle is repeated at a predetermined number of times after the second abnormality determination part determines that the power steering device is abnormal.

The invention claimed is:

1. A power steering device control device for a power steering device,
the power steering device including:
a steering mechanism configured to transmit rotation of a steering wheel to a steered wheel;
an electric motor configured to apply a steering force to the steering mechanism;
a transmission mechanism disposed between the steering mechanism and the electric motor, and configured to transmit a torque of the electric motor to the steering mechanism;
a housing configured to accommodate the transmission mechanism, the electric motor, and at least part of the steering mechanism;
a water sensing element disposed in the housing, and configured to sense water in the housing; and
a torque sensor configured to sense a steering torque occurring in the steering mechanism;
the power steering device control device comprising:
a motor command signal calculation part configured to calculate a motor command signal for control of driving of the electric motor, based on the steering torque;
a torque signal receiving part configured to receive input of a signal of the steering torque;
a motor rotational speed signal receiving part configured to receive input of a signal of rotational speed of the electric motor;
a steering speed signal receiving part configured to receive input of a signal of steering speed of the steering wheel;
a first abnormality determination part configured to determine that the power steering device is abnormal, based on one of the signals of the steering torque, the rotational speed of the electric motor, and the steering speed when steering operation is being performed; and
a second abnormality determination part configured to determine that the power steering device is abnormal, in response to detection of water by the water sensing element, wherein:
the first abnormality determination part includes:
an in-turning-state determination part configured to determine whether or not one of the signals of the steering torque, the rotational speed of the electric motor, and the steering speed when steering operation is performed to the steering wheel in a direction of further turn, has a periodic change in a predetermined frequency band; and
an in-returning-state determination part configured to sense a change of the steering torque in a predetermined region including a region in which the steering wheel is shifted from the direction of further turn to a direction of return; and
the first abnormality determination part is configured to determine that the power steering device is abnormal, based on a result of determination by one of the in-turning-state determination part and the in-returning-state determination part.

2. The power steering device control device as claimed in claim 1, wherein the first abnormality determination part is configured to determine that the power steering device is abnormal, in response to a condition that the in-turning-state determination part senses the periodic change and the in-returning-state determination part determines that the change of the steering torque is greater than or equal to a predetermined value.

3. The power steering device control device as claimed in claim 1, further comprising:
a warning light turn-on command signal output part configured to output a command signal to turn on a warning light of a vehicle in response to determination by the second abnormality determination part that the power steering device is abnormal; and
an application current quantity limiting part configured to limit an application current quantity to reduce a value of current flowing through the electric motor, in response to determination by the first abnormality determination part that the power steering device is abnormal.

4. The power steering device control device as claimed in claim 1, further comprising a command signal limiting part configured to limit the motor command signal, wherein the first abnormality determination part is further configured to stop determination of abnormality of the power steering device, when the motor command signal is limited by the command signal limiting part.

5. The power steering device control device as claimed in claim 1, wherein the first abnormality determination part is further configured to reduce a determination threshold value employed for determining that the power steering device is abnormal, in response to determination by the second abnormality determination part that the power steering device is abnormal.

6. The power steering device control device as claimed in claim 1, further comprising:
a first abnormality determination part use memory part configured to memorize an event that the first abnormality determination part determines that the power steering device is abnormal; and
a second abnormality determination part use memory part configured to memorize an event that the second abnormality determination part determines that the power steering device is abnormal;
wherein information memorized in the second abnormality determination part use memory part is cleared without clearance of information memorized in the first abnormality determination part use memory part, in response to occurrence of an abnormality in the second abnormality determination part use memory part.

7. The power steering device control device as claimed in claim 1, wherein the motor command signal calculation part is further configured to calculate the motor command signal in a manner to prevent a value of the motor command signal, which is actually outputted to the electric motor, from exceeding a value of the motor command signal that is calculated based on vehicle speed and the steering torque when the power steering device is normal, in response to determination by the second abnormality determination part that the power steering device is abnormal.

8. The power steering device control device as claimed in claim 1, further comprising an application current quantity limiting part configured to limit an application current quantity to reduce a value of current flowing through the electric motor, in response to determination by the first abnormality determination part that the power steering device is abnormal, wherein the application current quantity limiting part is configured to limit the application current quantity such that a limiting value of the application current quantity when abnormality of the power steering device is determined only by the first abnormality determination part is greater than that when abnormality of the power steering device is determined by both of the first abnormality determination part and the second abnormality determination part.

9. The power steering device control device as claimed in claim 1, wherein it is determined that determination of the second abnormality determination part is incorrect, unless the first abnormality determination part determines that the power steering device is abnormal, even after a predetermined time period elapses or after stop and start of a vehicle is repeated at a predetermined number of times after the second abnormality determination part determines that the power steering device is abnormal.

10. A power steering device comprising:
a steering mechanism configured to transmit rotation of a steering wheel to a steered wheel;
an electric motor configured to apply a steering force to the steering mechanism;
a transmission mechanism disposed between the steering mechanism and the electric motor, and configured to transmit a torque of the electric motor to the steering mechanism;
a housing configured to accommodate the transmission mechanism, the electric motor, and at least part of the steering mechanism;
a water sensing element disposed in the housing, and configured to sense water in the housing;
a torque sensor configured to sense a steering torque occurring in the steering mechanism; and
a control device configured to control driving of the electric motor;
the control device including:
a motor command signal calculation part configured to calculate a motor command signal for control of driving of the electric motor, based on the steering torque;
a torque signal receiving part configured to receive input of a signal of the steering torque;
a motor rotational speed signal receiving part configured to receive input of a signal of rotational speed of the electric motor;
a steering speed signal receiving part configured to receive input of a signal of steering speed of the steering wheel;
a first abnormality determination part configured to determine that the power steering device is abnormal, based on one of the signals of the steering torque, the rotational speed of the electric motor, and the steering speed when steering operation is being performed; and
a second abnormality determination part configured to determine that the power steering device is abnormal, in response to detection of water by the water sensing element, wherein:
the first abnormality determination part includes:
an in-turning-state determination part configured to determine whether or not one of the signals of the steering torque, the rotational speed of the electric motor, and the steering speed when steering operation is performed to the steering wheel in a direction of further turn, has a periodic change in a predetermined frequency band; and
an in-returning-state determination part configured to sense a change of the steering torque in a predetermined region including a region in which the steering wheel is shifted from the direction of further turn to a direction of return; and
the first abnormality determination part is configured to determine that the power steering device is abnormal, based on a result of determination by one of the in-turning-state determination part and the in-returning-state determination part.

11. The power steering device as claimed in claim 10, wherein the first abnormality determination part is configured to determine that the power steering device is abnormal, in response to a condition that the in-turning-state determination part senses the periodic change and the in-returning-state determination part determines that the change of the steering torque is greater than or equal to a predetermined value.

12. The power steering device as claimed in claim 10, further comprising:
a warning light turn-on command signal output part configured to output a command signal to turn on a warning light of a vehicle in response to determination by the second abnormality determination part that the power steering device is abnormal; and
an application current quantity limiting part configured to limit an application current quantity to reduce a value of current flowing through the electric motor, in response to determination by the first abnormality determination part that the power steering device is abnormal.

13. The power steering device as claimed in claim 10, further comprising a command signal limiting part configured to limit the motor command signal, wherein the first abnormality determination part is further configured to stop determination of abnormality of the power steering device, when the motor command signal is limited by the command signal limiting part.

14. The power steering device as claimed in claim 10, wherein the first abnormality determination part is further configured to reduce a determination threshold value employed for determining that the power steering device is abnormal, in response to determination by the second abnormality determination part that the power steering device is abnormal.

15. The power steering device as claimed in claim 10, further comprising:
a first abnormality determination part use memory part configured to memorize an event that the first abnormality determination part determines that the power steering device is abnormal; and
a second abnormality determination part use memory part configured to memorize an event that the second abnormality determination part determines that the power steering device is abnormal;
wherein information memorized in the second abnormality determination part use memory part is cleared without clearance of information memorized in the first abnormality determination part use memory part, in response to occurrence of an abnormality in the second abnormality determination part use memory part.

16. The power steering device as claimed in claim 10, wherein the motor command signal calculation part is further configured to calculate the motor command signal in a manner to prevent a value of the motor command signal, which is actually outputted to the electric motor, from exceeding a value of the motor command signal that is calculated based on vehicle speed and the steering torque when the power steering device is normal, in response to determination by the second abnormality determination part that the power steering device is abnormal.

17. The power steering device as claimed in claim 10, further comprising an application current quantity limiting part configured to limit an application current quantity to reduce a value of current flowing through the electric motor, in response to determination by the first abnormality determination part that the power steering device is abnormal, wherein the application current quantity limiting part is configured to limit the application current quantity such that a limiting value of the application current quantity when abnormality of the power steering device is determined only by the first abnormality determination part is greater than that when abnormality of the power steering device is determined by both of the first abnormality determination part and the second abnormality determination part.

18. The power steering device as claimed in claim 11, wherein it is determined that determination of the second abnormality determination part is incorrect, unless the first abnormality determination part determines that the power steering device is abnormal, even after a predetermined time period elapses or after stop and start of a vehicle is repeated at a predetermined number of times after the second abnormality determination part determines that the power steering device is abnormal.

* * * * *